US012673097B2

(12) United States Patent
Nakagami et al.

(10) Patent No.: US 12,673,097 B2
(45) Date of Patent: Jul. 7, 2026

(54) DNA VACCINE FOR SARS-COV-2

(71) Applicants: OSAKA UNIVERSITY, Suita (JP); TAKARA BIO INC., Kusatsu (JP); ANGES, INC., Ibaraki (JP)

(72) Inventors: Hironori Nakagami, Suita (JP); Ryuichi Morishita, Suita (JP); Hiroki Hayashi, Suita (JP); Yasunori Amaishi, Kusatsu (JP); Sachiko Okamoto, Kusatsu (JP); Junichi Mineno, Kusatsu (JP); Hisato Ikai, Ibaraki (JP); Junko Michibata, Ibaraki (JP); Takao Komatsuno, Ibaraki (JP)

(73) Assignees: OSAKA UNIVERSITY, Osaka (JP); TAKARA BIO INC., Shiga (JP); ANGES, INC., Osaka (JP)

( * ) Notice: Subject to any disclaimer, the term of this patent is extended or adjusted under 35 U.S.C. 154(b) by 627 days.

(21) Appl. No.: 18/028,613

(22) PCT Filed: Sep. 30, 2021

(86) PCT No.: PCT/JP2021/036255
§ 371 (c)(1),
(2) Date: Mar. 27, 2023

(87) PCT Pub. No.: WO2022/071513
PCT Pub. Date: Apr. 7, 2022

(65) Prior Publication Data
US 2023/0330214 A1     Oct. 19, 2023

(30) Foreign Application Priority Data
Oct. 2, 2020     (JP) ................................. 2020-167854

(51) Int. Cl.
| A61K 39/00 | (2006.01) |
| A61K 39/12 | (2006.01) |
| A61K 39/215 | (2006.01) |
| A61K 39/39 | (2006.01) |
| A61P 37/04 | (2006.01) |

(52) U.S. Cl.
CPC ........... *A61K 39/215* (2013.01); *A61P 37/04* (2018.01); *A61K 2039/53* (2013.01); *A61K 2039/55505* (2013.01)

(58) Field of Classification Search
CPC ...... A61K 2039/53; A61K 2039/55505; A61K 31/711; A61K 39/215; A61P 31/14
See application file for complete search history.

(56) References Cited

U.S. PATENT DOCUMENTS

| 2015/0202271 A1 | 7/2015 | Nakagami et al. |
| 2021/0299240 A1 | 9/2021 | Ueno et al. |

FOREIGN PATENT DOCUMENTS

| CN | 112575008 | 3/2021 |
| RU | 2 731 342 | 8/2020 |
| WO | 2014/034735 | 3/2014 |
| WO | 2018/074558 | 4/2018 |
| WO | 2018/075980 | 4/2018 |
| WO | 2018/189522 | 10/2018 |
| WO | 2021/076010 | 4/2021 |

OTHER PUBLICATIONS

International Search Report issued Oct. 26, 2021 in corresponding International (PCT) Patent Application No. PCT/JP2021/036255.
English language translation of International Preliminary Report on Patentability issued Mar. 28, 2023 in corresponding International (PCT) Patent Application No. PCT/JP2021/036255.
Database GenBank [online], Accession No. NC_045512, Jul. 2020 [retrieved on Oct. 15, 2021], Internet: <URL: https://www.ncbi.nlm.nih.gov/nuccore/NC_045512> in particular, amino acid sequence for "spike glycoprotein".
Online. [online], Mar. 27, 2020 [retrieved on Oct. 15, 2021], Internet: <URL: https://bio.nikkeibp.co.jp/atcl/news/pl/20/03/26/06735/?ST=print>, pp. 1-4, (Kubota, Aya. Nikkei Biotechnology & Business Online), non-official translation (AnGes President Yamada Clarifies Status of Development of Covid-19 DNA Vaccine.) in particular, p. 2, line 4 from the bottom, with English language translation.

*Primary Examiner* — Barry A Chestnut
(74) *Attorney, Agent, or Firm* — Wenderoth, Lind & Ponack, L.L.P.

(57) ABSTRACT

Provided is DNA that: encodes a coronavirus (SARS COV-2) spike protein or a fragment thereof; and has been optimized to partially or fully exhibit a codon included in a DNA sequence.

9 Claims, 4 Drawing Sheets

Specification includes a Sequence Listing.

SEQUENCE LISTING

<160> NUMBER OF SEQ ID NOS: 18

<210> SEQ ID NO 1
<211> LENGTH: 1273
<212> TYPE: PRT
<213> ORGANISM: SARS-CoV-2

-continued

```
<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415
```

```
Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
            450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
            530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830
```

-continued

```
Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
            995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
```

-continued

```
         1235            1240            1245

Ser Cys  Gly Ser Cys Cys Lys  Phe Asp Glu Asp Asp  Ser Glu Pro
         1250            1255            1260

Val Leu  Lys Gly Val Lys Leu  His Tyr Thr
         1265            1270

<210> SEQ ID NO 2
<211> LENGTH: 3822
<212> TYPE: DNA
<213> ORGANISM: SARS-CoV-2

<400> SEQUENCE: 2
atgtttgttt ttcttgtttt attgccacta gtctctagtc agtgtgttaa tcttacaacc        60
agaactcaat taccccctgc atacactaat tctttcacac gtggtgtttta ttaccctgac       120 aaagttttca gatcctcagt tttacattca actcaggact tgttcttacc tttcttttcc       180
aatgttactt ggttccatgc tatacatgtc tctgggacca atggtactaa gaggtttgat       240
aaccctgtcc taccatttaa tgatggtgtt tattttgctt ccactgagaa gtctaacata       300
ataagaggct ggattttttgg tactacttta gattcgaaga cccagtccct acttattgtt       360
aataacgcta ctaatgttgt tattaaagtc tgtgaatttc aattttgtaa tgatccattt       420
ttgggtgttt attaccacaa aaacaacaaa agttggatgg aaagtgagtt cagagtttat       480
tctagtgcga ataattgcac ttttgaatat gtctctcagc cttttcttat ggaccttgaa       540
ggaaaacagg gtaatttcaa aaatcttagg gaatttgtgt ttaagaatat tgatggttat       600
tttaaaatat attctaagca cacgcctatt aatttagtgc gtgatctccc tcagggtttt       660
tcggctttag aaccattggt agatttgcca ataggtatta acatcactag gtttcaaact       720
ttacttgctt tacatagaag ttatttgact cctggtgatt cttcttcagg ttggacagct       780
ggtgctgcag cttattatgt gggttatctt caacctagga ctttttctatt aaaatataat       840 gaaaatggaa ccattacaga tgctgtagac tgtgcacttg accctctctc agaaacaaag       900
tgtacgttga atccttcac tgtagaaaaa ggaatctatc aaacttctaa ctttagagtc       960
caaccaacag aatctattgt tagatttcct aatattacaa acttgtgccc ttttggtgaa      1020
gtttttaacg ccaccagatt tgcatctgtt tatgcttgga acaggaagag aatcagcaac      1080
tgtgttgctg attattctgt cctatataat tccgcatcat tttccacttt taagtgttat      1140
ggagtgtctc ctactaaatt aaatgatctc tgctttacta atgtctatgc agattcattt      1200
gtaattagag gtgatgaagt cagacaaatc gctccagggc aaactggaaa gattgctgat      1260
tataattata aattaccaga tgattttaca ggctgcgtta tagcttggaa ttctaacaat      1320
cttgattcta aggttggtgg taattataat tacctgtata gattgtttag gaagtctaat      1380
ctcaaacctt ttgagagaga tatttcaact gaaatctatc aggccggtag cacaccttgt      1440
aatggtgttg aaggttttaa ttgttacttt cctttacaat catatggttt ccaacccact      1500
aatggtgttg gttaccaacc atacagagta gtagtacttt cttttgaact ctacatgca      1560 ccagcaactg tttgtggacc taaaaagtct actaatttgg ttaaaaacaa atgtgtcaat      1620
ttcaacttca atggtttaac aggcacaggt gttcttactg agtctaacaa aaagtttctg      1680
cctttccaac aatttggcag agacattgct gacactactg atgctgtccg tgatccacag      1740
acacttgaga ttcttgacat tacaccatgt tctttttggtg tgtcagtgt tataacacca      1800 ggaacaaata cttctaacca ggttgctgtt ctttatcagg atgttaactg cacagaagtc      1860
cctgttgcta ttcatgcaga tcaacttact cctacttggc gtgtttattc tacaggttct      1920
```

```
aatgttttc aaacacgtgc aggctgttta atagggctg aacatgtcaa caactcatat      1980
gagtgtgaca tacccattgg tgcaggtata tgcgctagtt atcagactca gactaattct      2040
cctcggcggg cacgtagtgt agctagtcaa tccatcattg cctacactat gtcacttggt      2100
gcagaaaatt cagttgctta ctctaataac tctattgcca tacccacaaa ttttactatt      2160
agtgttacca cagaaattct accagtgtct atgaccaaga catcagtaga ttgtacaatg      2220
tacatttgtg gtgattcaac tgaatgcagc aatcttttgt tgcaatatgg cagtttttgt      2280
acacaattaa accgtgcttt aactggaata gctgttgaac aagacaaaaa cacccaagaa      2340
gtttttgcac aagtcaaaca aatttacaaa acaccaccaa ttaaagattt tggtggtttt      2400
aatttttcac aaatattacc agatccatca aaaccaagca agaggtcatt tattgaagat      2460 ctactttca acaaagtgac acttgcagat gctggcttca tcaaacaata tggtgattgc      2520
cttggtgata ttgctgctag agacctcatt tgtgcacaaa agtttaacgg ccttactgtt      2580
ttgccacctt tgctcacaga tgaaatgatt gctcaataca cttctgcact gttagcgggt      2640
acaatcactt ctggttggac ctttggtgca ggtgctgcat tacaaatacc atttgctatg      2700
caaatggctt ataggtttaa tggtattgga gttacacaga atgttctcta tgagaaccaa      2760
aaattgattg ccaaccaatt taatagtgct attggcaaaa ttcaagactc actttcttcc      2820
acagcaagtg cacttggaaa acttcaagat gtggtcaacc aaaatgcaca agctttaaac      2880
acgcttgtta acaacttag ctccaatttt ggtgcaattt caagtgtttt aaatgatatc      2940
ctttcacgtc ttgacaaagt tgaggctgaa gtgcaaattg ataggttgat cacaggcaga      3000
cttcaaagtt tgcagacata tgtgactcaa caattaatta gagctgcaga aatcagagct      3060
tctgctaatc ttgctgctac taaaatgtca gagtgtgtac ttggacaatc aaaaagagtt      3120 gattttgtg gaaagggcta tcatcttatg tccttccctc agtcagcacc tcatggtgta      3180
gtcttcttgc atgtgactta tgtccctgca caagaaaaga acttcacaac tgctcctgcc      3240
atttgtcatg atggaaaagc acactttcct cgtgaaggtg tctttgtttc aaatggcaca      3300
cactggtttg taacacaaag gaattttat gaaccacaaa tcattactac agacaacaca      3360
tttgtgtctg gtaactgtga tgttgtaata ggaattgtca acaacacagt ttatgatcct      3420
ttgcaacctg aattagactc attcaaggag gagttagata aatatttaa gaatcataca      3480 tcaccagatg ttgatttagg tgacatctct ggcattaatg cttcagttgt aaacattcaa      3540
aaagaaattg accgcctcaa tgaggttgcc aagaatttaa atgaatctct catcgatctc      3600
caagaacttg gaaagtatga gcagtatata aaatggccat ggtacatttg ctaggtttt      3660 atagctggct tgattgccat agtaatggtg acaattatgc tttgctgtat gaccagttgc      3720
tgtagttgtc tcaagggctg ttgttcttgt ggatcctgct gcaaatttga tgaagacgac      3780
tctgagccag tgctcaaagg agtcaaatta cattacacat aa      3822
```

<210> SEQ ID NO 3
<211> LENGTH: 3822
<212> TYPE: DNA
<213> ORGANISM: Artificial
<220> FEATURE:
<223> OTHER INFORMATION: Codon-modified DNA sequence coding SARS-CoV-2
      spike protein

<400> SEQUENCE: 3

```
atgttcgtgt cctggtgct gctgcccctg gtgagcagcc agtgcgtgaa cctgaccacc        60
agaacccagc tgcccccgc ctacaccaac agcttcacca gaggcgtgta ctaccccgac       120
```

-continued

```
aaggtgttca gaagcagcgt gctgcacagc acccaggacc tgttcctgcc cttcttcagc      180
aacgtgacct ggttccacgc catccacgtg agcggcacca acggcaccaa gagattcgac      240
aaccccgtgc tgcccttcaa cgacggcgtg tacttcgcca gcaccgagaa gagcaacatc      300
atcagaggct ggatcttcgg caccaccctg gacagcaaga cccagagcct gctgatcgtg      360
aacaacgcca ccaacgtggt gatcaaggtg tgcgagttcc agttctgcaa cgaccccttc      420
ctgggcgtgt actaccacaa gaacaacaag agctggatgg agagcgagtt cagagtgtac      480
agcagcgcca caactgcac cttcgagtac gtgagccagc ccttcctgat ggacctggag        540
ggcaagcagg gcaacttcaa gaacctgaga gagttcgtgt tcaagaacat cgacggctac      600
ttcaagatct acagcaagca cacccccatc aacctggtga gagacctgcc tcagggcttt      660
agcgccctgg agccactggt ggacctgcca atcggcatca acatcaccag attccagacc      720
ctgctggccc tgcacagaag ctacctgaca ccaggcgatt ctagctctgg atggacagcc      780
ggcgccgctg cctattacgt gggctacctg cagcctagaa ccttcctgct gaagtacaac      840
gagaacggca ccatcaccga tgccgtggac tgcgccctgg atcccctgag cgagaccaag      900
tgtaccctga gagcttcac cgtggagaag ggcatctacc agaccagcaa cttcagagtg        960
cagcccaccg agagcatcgt gagattcccc aacatcacca acctgtgccc cttcggcgag      1020
gtgttcaacg ccaccagatt cgccagcgtg tacgcctgga acagaaagag aatcagcaac      1080
tgcgtggccg actacagcgt gctgtacaac agcgccagct tcagcacctt caagtgctac      1140
ggcgtgagcc ccaccaagct gaacgacctg tgcttcacca acgtgtacgc cgacagcttc      1200
gtgatcagag cgacgaggt gagacagatt gcccctggcc agaccggcaa gatcgccgac        1260
tacaactaca agctgcccga cgacttcacc ggctgcgtga tcgcctggaa cagcaacaac      1320
ctggacagca aggtgggcgg caactacaac tacctgtaca gactgttcag aaagagcaac      1380
ctgaagccct tcgagagaga catcagcacc gagatctacc aggccggctc tacccccatgc     1440 aatggcgtgg agggcttcaa ttgctacttc cccctgcaga gctacggctt ccagcccacc      1500
aacggcgtgg gctaccagcc ctacagagtg gtggtgctga gctttgaact gctgcacgcc      1560
cctgccaccg tgtgcggccc aaagaagagc accaatctgg tgaagaacaa gtgcgtgaac      1620
ttcaacttca cggcctgac cggcaccggc gtgctgaccg agagcaacaa gaagttcctg        1680
cccttccagc agtccggcag agacatcgcc gacaccaccg atgccgtgag agatccccag      1740
accctggaga tcctggacat cacccccctgt agctttggcg gcgtgagcgt gattacccc        1800 ggcaccaata ccagcaacca ggtggccgtg ctgtaccagg acgtgaactg caccgaggtg       1860
ccagtggcca tccatgccga ccagctgacc ccaacctgga gagtgtacag caccggcagc      1920
aacgtgttcc agacaagagc cggctgtctg attggcgccg agcacgtgaa taacagctac      1980
gagtgcgata tcccaatcgg cgccggcatc tgtgccagct atcagaccca gaccaatagc      2040
cccagaagag ccagaagcgt ggccagccag agcatcatcg cctacaccat gagcctgggc      2100
gccgagaaca gcgtggccta cagcaacaac agcatcgcca tccccaccaa cttcaccatc      2160
agcgtgacca ccgagatcct gccgtgagc atgaccaaga ccagcgtgga ctgcaccatg        2220
tacatctgcg gcgacagcac cgagtgcagc aacctgctgc tgcagtacgg cagcttctgc      2280
acccagctga acagagccct gaccggcatc gccgtggagc aggacaagaa cacccaggag      2340
gtgttcgccc aggtgaagca gatctacaag acccccccca tcaaggactt cggcggcttc      2400
aacttcagcc agatcctgcc cgaccccagc aagcccagca gagaagctt catcgaggac        2460
```

-continued

```
ctgctgttca acaaggtgac cctggccgac gccggcttca tcaagcagta cggcgactgc    2520
ctgggcgaca tcgccgccag agacctgatc tgcgcccaga agtttaatgg actgacagtg    2580
ctgccacccc tgctgaccga tgagatgatc gcccagtaca ccagcgctct gctggccggc    2640
acaatcacca gcggctggac atttggagcc ggagccgctc tgcagatccc atttgccatg    2700
cagatggcct acagattcaa cggcatcggc gtgacccaga acgtgctgta cgagaaccag    2760
aagctgatcg ccaaccagtt caacagcgcc atcggcaaga tccaggacag cctgtctagc    2820
acagcctctg ccctgggcaa gctgcaggat gtggtgaacc agaacgccca ggccctgaac    2880
accctggtga agcagctgag cagcaacttc ggcgccatca gcagcgtgct gaacgacatc    2940
ctgagcagac tggacaaggt ggaggccgag gtgcagatcg acagactgat caccggcaga    3000
ctgcagagcc tgcagaccta cgtgacccag cagctgatca gagccgccga aatcagagcc    3060
agcgccaatc tggccgccac caagatgagc gagtgcgtgc tgggccagag caagagagtg    3120
gacttctgcg gcaagggcta ccacctgatg agctttcccc agagcgcccc tcacggcgtg    3180
gtgtttctgc acgtgaccta cgtgcctgcc caggagaaga acttcaccac cgcccctgcc    3240
atctgccacg atggcaaggc ccacttccct agagagggcg tgttcgtgag caacggcacc    3300
cactggttcg tgacccagag aaacttctac gagccccaga tcatcaccac cgacaacacc    3360
ttcgtgagcg gcaactgcga cgtggtgatc ggcatcgtga acaacaccgt gtacgacccc    3420
ctgcagcccg agctggacag cttcaaggag gagctggaca agtacttcaa gaaccacacc    3480
agccccgatg tggacctggg cgatatcagc ggcatcaatg ccagcgtggt gaacatccag    3540
aaggagatcg accggctcaa tgaggtggcc aagaacctga cgagagcct gatcgacctg    3600 caggaactgg gcaaatatga gcagtacatc aagtggccct ggtacatctg gctgggcttc    3660
atcgccggcc tgatcgccat cgtgatggtg accatcatgc tgtgctgcat gaccagctgc    3720
tgcagctgcc tgaagggctg ctgcagctgc gggtcttgtt gcaagttcga cgaggacgac    3780
agcgagcccg tgctgaaggg cgtgaagctg cactacacct aa    3822
```

```
<210> SEQ ID NO 4
<211> LENGTH: 6734
<212> TYPE: DNA
<213> ORGANISM: Artificial
<220> FEATURE:
<223> OTHER INFORMATION: Plasmid CO

<400> SEQUENCE: 4
gctgcttcgc gatgtacggg ccagatatac gcgttgacat tgattattga ctagttatta    60
atagtaatca attacggggt cattagttca tagcccatat atggagttcc gcgttacata    120
acttacggta aatggcccgc ctggctgacc gcccaacgac ccccgcccat tgacgtcaat    180
aatgacgtat gttcccatag taacgccaat agggactttc cattgacgtc aatgggtgga    240
gtatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag ccaccatgtt cgtgttcctg    720
```

-continued

```
gtgctgctgc ccctggtgag cagccagtgc gtgaacctga ccaccagaac ccagctgccc      780
cccgcctaca ccaacagctt caccagaggc gtgtactacc ccgacaaggt gttcagaagc      840
agcgtgctgc acagcacccca ggacctgttc ctgcccttct tcagcaacgt gacctggttc      900
cacgccatcc acgtgagcgg caccaacggc accaagagat tcgacaaccc cgtgctgccc      960
ttcaacgacg gcgtgtactt cgccagcacc gagaagagca acatcatcag aggctggatc      1020
ttcggcacca ccctggacag caagacccag agcctgctga tcgtgaacaa cgccaccaac      1080
gtggtgatca aggtgtgcga gttccagttc tgcaacgacc ccttcctggg cgtgtactac      1140
cacaagaaca caaagagctg gatggagagc gagttcagag tgtacagcag cgccaacaac      1200
tgcaccttcg agtacgtgag ccagcccttc ctgatggacc tggagggcaa gcagggcaac      1260
ttcaagaacc tgagagagtt cgtgttcaag aacatcgacg gctacttcaa gatctacagc      1320
aagcacaccc ccatcaacct ggtgagagac ctgcctcagg gctttagcgc cctggagcca      1380
ctggtggacc tgccaatcgg catcaacatc accagattcc agaccctgct ggccctgcac      1440
agaagctacc tgacaccagg cgattctagc tctggatgga cagccggcgc cgctgcctat      1500
tacgtgggct acctgcagcc tagaaccttc ctgctgaagt acaacgagaa cggcaccatc      1560
accgatgccg tggactgcgc cctggatccc ctgagcgaga ccaagtgtac cctgaagagc      1620
ttcaccgtgg agaagggcat ctaccagacc agcaacttca gagtgcagcc caccgagagc      1680
atcgtgagat tccccaacat caccaacctg tgccccttcg gcgaggtgtt caacgccacc      1740
agattcgcca gcgtgtacgc ctggaacaga aagagaatca gcaactgcgt ggccgactac      1800
agcgtgctgt acaacagcgc cagcttcagc accttcaagt gctacggcgt gagcccacc      1860 aagctgaacg acctgtgctt caccaacgtg tacgccgaca gcttcgtgat cagaggcgac      1920
gaggtgagac agattgcccc tggccagacc ggcaagatcg ccgactacaa ctacaagctg      1980
cccgacgact tcaccggctg cgtgatcgcc tggaacagca caacctgga cagcaaggtg      2040 ggcggcaact acaactacct gtacagactg ttcagaaaga gcaacctgaa gcccttcgag      2100
agagacatca gcaccgagat ctaccaggcc ggctctaccc catgcaatgg cgtggagggc      2160
ttcaattgct acttcccct gcagagctac ggcttccagc ccaccaacgg cgtgggctac      2220
cagccctaca gagtggtggt gctgagcttt gaactgctgc acgcccctgc caccgtgtgc      2280
ggcccaaaga gagcaccaa tctggtgaag aacaagtgcg tgaacttcaa cttcaacggc      2340
ctgaccggca ccggcgtgct gaccgagagc aacaagaagt tcctgccctt ccagcagttc      2400
ggcagagaca tcgccgacac caccgatgcc gtgagagatc cccagaccct ggagatcctg      2460
gacatcaccc cctgtagctt tggcggcgtg agcgtgatta cccccggcac caataccagc      2520
aaccaggtgg ccgtgctgta ccaggacgtg aactgcaccg aggtgccagt ggccatccat      2580
gccgaccagc tgacccccaac ctggagagtg tacagcaccg gcagcaacgt gttccagaca      2640
agagccggct gtctgattgg cgccgagcac gtgaataaca gctacgagtg cgatatccca      2700
atcggcgccg gcatctgtgc cagctatcag acccagacca atagccccag aagagccaga      2760
agcgtggcca ccagagcat catcgcctac accatgagcc tgggcgccga aacagcgtg      2820 gcctacagca acaacagcat cgccatcccc accaacttca ccatcagcgt gaccaccgag      2880
atcctgcccg tgagcatgac caagaccagc gtggactgca ccatgtacat ctgcggcgac      2940
agcaccgagt gcagcaacct gctgctgcag tacggcagct tctgcaccca gctgaacaga      3000
gccctgaccg gcatcgccgt gggagcaggac aagaacaccc aggaggtgtt cgcccaggtg      3060
```

-continued

```
aagcagatct acaagacccc ccccatcaag gacttcggcg gcttcaactt cagccagatc   3120
ctgcccgacc ccagcaagcc cagcaagaga agcttcatcg aggacctgct gttcaacaag   3180
gtgaccctgg ccgacgccgg cttcatcaag cagtacggcg actgcctggg cgacatcgcc   3240
gccagagacc tgatctgcgc ccagaagttt aatggactga cagtgctgcc acccctgctg   3300
accgatgaga tgatcgccca gtacaccagc gctctgctgg ccggcacaat caccagcggc   3360
tggacatttg gagccggagc cgctctgcag atcccatttg ccatgcagat ggcctacaga   3420
ttcaacggca tcggcgtgac ccagaacgtg ctgtacgaga accagaagct gatcgccaac   3480
cagttcaaca cgcgccatcgg caagatccag gacagcctgt ctagcacagc ctctgccctg   3540
ggcaagctgc aggatgtggt gaaccagaac gcccaggccc tgaacaccct ggtgaagcag   3600
ctgagcagca acttcggcgc catcagcagc gtgctgaacg acatcctgag cagactggac   3660
aaggtggagg ccgaggtgca gatcgacaga ctgatcaccg gcagactgca gagcctgcag   3720
acctacgtga cccagcagct gatcagagcc gccgaaatca gagccagcgc caatctggcc   3780
gccaccaaga tgagcgagtg cgtgctgggc cagagcaaga gagtggactt ctgcggcaag   3840
ggctaccacc tgatgagctt tccccagagc gcccctcacg gcgtggtgtt tctgcacgtg   3900
acctacgtgc ctgcccagga gaagaacttc accaccgccc ctgccatctg ccacgatggc   3960
aaggcccact ccctagaga gggcgtgttc gtgagcaacg gcacccactg gttcgtgacc   4020
cagagaaact tctacgagcc ccagatcatc accaccgaca acacccttcgt gagcggcaac   4080 tgcgacgtgg tgatcggcat cgtgaacaac accgtgtacg accccctgca gcccgagctg   4140
gacagcttca aggaggagct ggacaagtac ttcaagaacc acaccagccc cgatgtggac   4200
ctgggcgata tcagcggcat caatgccagc gtggtgaaca tccagaagga gatcgaccgg   4260
ctcaatgagg tggccaagaa cctgaacgag agcctgatcg acctgcagga actgggcaaa   4320
tatgagcagt acatcaagtg gccctggtac atctggctgg gcttcatcgc cggcctgatc   4380
gccatcgtga tggtgaccat catgctgtgc tgcatgacca gctgctgcag ctgcctgaag   4440
ggctgctgca gctgcgggtc ttgttgcaag ttcgacgagg acgacagcga gcccgtgctg   4500
aagggcgtga agctgcacta cacctaatct agagggcccg tttaaacccg ctgatcagcc   4560
tcgactgtgc cttctagttg ccagccatct gttgtttgcc cctcccccgt gccttccttg   4620
accctggaag gtgccactcc cactgtcctt tcctaataaa atgaggaaat tgcatcgcat   4680
tgtctgagta ggtgtcattc tattctgggg ggtggggtgg ggcaggacag caagggggag   4740
gattgggaag acaatagcag gcatgctggg gatgcggtgg gctctatggc ttctactggg   4800
cggttttatg gacagcaagc gaaccggaat tgccagctgg ggcgccctct ggtaaggttg   4860
ggaagccctg caaagtaaac tggatggctt tcttgccgcc aaggatctga tggcgcaggg   4920
gatcaagctc tgatcaagag acaggatgag gatcgtttcg catgattgaa caagatggat   4980
tgcacgcagg ttctccggcc gcttgggtgg agaggctatt cggctatgac tgggcacaac   5040
agacaatcgg ctgctctgat gccgccgtgt tccggctgtc agcgcagggg cgcccggttc   5100
tttttgtcaa gaccgacctg tccggtgccc tgaatgaact gcaagacgag gcagcgcggc   5160
tatcgtggct ggccacgacg ggcgttcctt gcgcagctgt gctcgacgtt gtcactgaag   5220
cgggaaggga ctggctgcta ttgggcgaag tgccggggca ggatctcctg tcatctcacc   5280
ttgctcctgc cgagaaagta tccatcatgg ctgatgcaat gcggcggctg catacgcttg   5340
atccggctac ctgcccattc gaccaccaag cgaaacatcg catcgagcga gcacgtactc   5400
ggatggaagc cggtcttgtc gatcaggatg atctggacga agagcatcag gggctcgcgc   5460
```

```
cagccgaact gttcgccagg ctcaaggcga gcatgcccga cggcgaggat ctcgtcgtga      5520
cccatggcga tgcctgcttg ccgaatatca tggtggaaaa tggccgcttt tctggattca      5580
tcgactgtgg ccggctgggt gtggcggacc gctatcagga catagcgttg gctacccgtg      5640
atattgctga agagcttggc ggcgaatggg ctgaccgctt cctcgtgctt tacggtatcg      5700
ccgctcccga ttcgcagcgc atcgccttct atcgccttct tgacgagttc ttctgaatta      5760
ttaacgctta caatttcctg atgcggtatt ttctccttac gcatctgtgc ggtatttcac      5820
accgcatcag gtggcacttt tcggggaaat gtgcgcggaa cccctatttg tttatttttc      5880
taaatacatt caaatatgta tccgctcatg agacaataac cctgataaat gcttcaataa      5940
tagcacgtgc taaaacttca tttttaattt aaaaggatct aggtgaagat cctttttgat      6000
aatctcatga ccaaaatccc ttaacgtgag ttttcgttcc actgagcgtc agaccccgta      6060
gaaaagatca aggatcttc ttgagatcct tttttttctgc gcgtaatctg ctgcttgcaa      6120
acaaaaaaac caccgctacc agcggtggtt tgtttgccgg atcaagagct accaactctt      6180
tttccgaagg taactggctt cagcagagcg cagataccaa atactgttct tctagtgtag      6240
ccgtagttag gccaccactt caagaactct gtagcaccgc ctacatacct cgctctgcta      6300
atcctgttac cagtggctgc tgccagtggc gataagtcgt gtcttaccgg gttggactca      6360
agacgatagt taccggataa ggcgcagcgg tcgggctgaa cggggggttc gtgcacacag      6420
cccagcttgg agcgaacgac ctacaccgaa ctgagatacc tacagcgtga gctatgagaa      6480
agcgccacgc ttcccgaagg gagaaaggcg gacaggtatc cggtaagcgg cagggtcgga      6540
acaggagagc gcacgaggga gcttccaggg ggaaacgcct ggtatcttta tagtcctgtc      6600
gggtttcgcc acctctgact tgagcgtcga ttttgtgat gctcgtcagg ggggcggagc      6660
ctatggaaaa acgccagcaa cgcggccttt ttacggttcc tggccttttg ctggcctttt      6720
gctcacatgt tctt                                                       6734
```

```
<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
ctacatgcac cagcaactgt                                                   20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
cacctgtgcc tgttaaacca                                                   20

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
```

-continued agccagagca tcatcgccta                                                    20

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
tggtcacgct gatggtgaag                                                    20

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
gcaccgtcaa ggctgagaac                                                    20

<210> SEQ ID NO 10
<211> LENGTH: 19
<212> TYPE: DNA
<213> ORGANISM: Artificial
<220> FEATURE:
<223> OTHER INFORMATION: Primer

<400> SEQUENCE: 10
tggtgaagac gccagtgga                                                     19

<210> SEQ ID NO 11
<211> LENGTH: 1254
<212> TYPE: PRT
<213> ORGANISM: Artificial
<220> FEATURE:
<223> OTHER INFORMATION: An amino acid sequence of modified SARS-CoV-2
      spike protein (4GP)

<400> SEQUENCE: 11

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

-continued

```
Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
        180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
        290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
```

-continued

```
              580               585                590

Gly Gly Val Ser Val Ile Thr Pro Gly Thr Asn Thr Ser Asn Gln Val
         595               600               605

Ala Val Leu Tyr Gln Gly Val Asn Cys Thr Glu Val Pro Val Ala Ile
         610               615               620

His Ala Asp Gln Leu Thr Pro Thr Trp Arg Val Tyr Ser Thr Gly Ser
625               630               635               640

Asn Val Phe Gln Thr Arg Ala Gly Cys Leu Ile Gly Ala Glu His Val
             645               650               655

Asn Asn Ser Tyr Glu Cys Asp Ile Pro Ile Gly Ala Gly Ile Cys Ala
             660               665               670

Ser Tyr Gln Thr Gln Thr Asn Ser Pro Arg Arg Ala Arg Ser Val Ala
         675               680               685

Ser Gln Ser Ile Ile Ala Tyr Thr Met Ser Leu Gly Ala Glu Asn Ser
         690               695               700

Val Ala Tyr Ser Asn Asn Ser Ile Ala Ile Pro Thr Asn Phe Thr Ile
705               710               715               720

Ser Val Thr Thr Glu Ile Leu Pro Val Ser Met Thr Lys Thr Ser Val
             725               730               735

Asp Cys Thr Met Tyr Ile Cys Gly Asp Ser Thr Glu Cys Ser Asn Leu
             740               745               750

Leu Leu Gln Tyr Gly Ser Phe Cys Thr Gln Leu Asn Arg Ala Leu Thr
         755               760               765

Gly Ile Ala Val Glu Gln Asp Lys Asn Thr Gln Glu Val Phe Ala Gln
         770               775               780

Val Lys Gln Ile Tyr Lys Thr Pro Pro Ile Lys Asp Phe Gly Gly Phe
785               790               795               800

Asn Phe Ser Gln Ile Leu Pro Asp Pro Ser Lys Pro Ser Lys Arg Ser
             805               810               815

Phe Ile Glu Asp Leu Leu Phe Asn Lys Val Thr Leu Ala Asp Ala Gly
             820               825               830

Phe Ile Lys Gln Tyr Gly Asp Cys Leu Gly Asp Ile Ala Ala Arg Asp
         835               840               845

Leu Ile Cys Ala Gln Lys Phe Asn Gly Leu Thr Val Leu Pro Pro Leu
         850               855               860

Leu Thr Asp Glu Met Ile Ala Gln Tyr Thr Ser Ala Leu Leu Ala Gly
865               870               875               880

Thr Ile Thr Ser Gly Trp Thr Phe Gly Ala Gly Ala Ala Leu Gln Ile
             885               890               895

Pro Phe Ala Met Gln Met Ala Tyr Arg Phe Asn Gly Ile Gly Val Thr
             900               905               910

Gln Asn Val Leu Tyr Glu Asn Gln Lys Leu Ile Ala Asn Gln Phe Asn
         915               920               925

Ser Ala Ile Gly Lys Ile Gln Asp Ser Leu Ser Ser Thr Ala Ser Ala
         930               935               940

Leu Gly Lys Leu Gln Asp Val Val Asn Gln Asn Ala Gln Ala Leu Asn
945               950               955               960

Thr Leu Val Lys Gln Leu Ser Ser Asn Phe Gly Ala Ile Ser Ser Val
             965               970               975

Leu Asn Asp Ile Leu Ser Arg Leu Asp Pro Pro Glu Ala Glu Val Gln
             980               985               990

Ile Asp Arg Leu Ile Thr Gly Arg  Leu Gln Ser Leu Gln  Thr Tyr Val
         995               1000              1005
```

-continued

```
Thr Gln  Gln Leu Ile Arg Ala  Ala Glu Ile Arg Ala  Ser Ala Asn
    1010              1015              1020

Leu Ala  Ala Thr Lys Met Ser  Glu Cys Val Leu Gly  Gln Ser Lys
    1025              1030              1035

Arg Val  Asp Phe Cys Gly Lys  Gly Tyr His Leu Met  Ser Phe Pro
    1040              1045              1050

Gln Ser  Ala Pro His Gly Val  Val Phe Leu His Val  Thr Tyr Val
    1055              1060              1065

Pro Ala  Gln Glu Lys Asn Phe  Thr Thr Ala Pro Ala  Ile Cys His
    1070              1075              1080

Asp Gly  Lys Ala His Phe Pro  Arg Glu Gly Val Phe  Val Ser Asn
    1085              1090              1095

Gly Thr  His Trp Phe Val Thr  Gln Arg Asn Phe Tyr  Glu Pro Gln
    1100              1105              1110

Ile Ile  Thr Thr Asp Asn Thr  Phe Val Ser Gly Asn  Cys Asp Val
    1115              1120              1125

Val Ile  Gly Ile Val Asn Asn  Thr Val Tyr Asp Pro  Leu Gln Pro
    1130              1135              1140

Glu Leu  Asp Ser Phe Lys Glu  Glu Leu Asp Lys Tyr  Phe Lys Asn
    1145              1150              1155

His Thr  Ser Pro Asp Val Asp  Leu Gly Asp Ile Ser  Gly Ile Asn
    1160              1165              1170

Ala Ser  Val Val Asn Ile Gln  Lys Glu Ile Asp Arg  Leu Asn Glu
    1175              1180              1185

Val Ala  Lys Asn Leu Asn Glu  Ser Leu Ile Asp Leu  Gln Glu Leu
    1190              1195              1200

Gly Lys  Tyr Glu Gln Tyr Ile  Lys Trp Pro Trp Tyr  Ile Trp Leu
    1205              1210              1215

Gly Phe  Ile Ala Gly Leu Ile  Ala Ile Val Met Val  Thr Ile Met
    1220              1225              1230

Leu Cys  Cys Met Thr Ser Cys  Cys Ser Cys Leu Lys  Gly Cys Cys
    1235              1240              1245

Ser Cys  Gly Ser Cys Cys
    1250
```

```
<210> SEQ ID NO 12
<211> LENGTH: 3765
<212> TYPE: DNA
<213> ORGANISM: Artificial
<220> FEATURE:
<223> OTHER INFORMATION: A nucleotide sequence coding modified
      SARS-CoV-2 spike protein (4GP)

<400> SEQUENCE: 12
atgttcgtgt tcctggtgct gctgcccctg gtgagcagcc agtgcgtgaa cctgaccacc      60
agaacccagc tgccccccgc ctacaccaac agcttcacca gaggcgtgta ctaccccgac     120
aaggtgttca gaagcagcgt gctgcacagc acccaggacc tgttcctgcc cttcttcagc     180
aacgtgacct ggttccacgc catccacgtg agcggcacca acggcaccaa gagattcgac     240
aaccccgtgc tgcccttcaa cgacggcgtg tacttcgcca gcaccgagaa gagcaacatc     300
atcagaggct ggatcttcgg caccaccctg gacagcaaga cccagagcct gctgatcgtg     360
aacaacgcca ccaacgtggt gatcaaggtg tgcgagttcc agttctgcaa cgacccttc      420 ctgggcgtgt actaccacaa gaacaacaag agctggatgg agagcgagtt cagagtgtac     480
```

-continued

```
agcagcgcca acaactgcac cttcgagtac gtgagccagc ccttcctgat ggacctggag      540
ggcaagcagg gcaacttcaa gaacctgaga gagttcgtgt tcaagaacat cgacggctac      600
ttcaagatct acagcaagca cacccccatc aacctggtga gagacctgcc tcagggcttt      660
agcgccctgg agccactggt ggacctgcca atcggcatca acatcaccag attccagacc      720
ctgctggccc tgcacagaag ctacctgaca ccaggcgatt ctagctctgg atggacagcc      780
ggcgccgctg cctattacgt gggctacctg cagcctagaa ccttcctgct gaagtacaac      840
gagaacggca ccatcaccga tgccgtggac tgcgccctgg atcccctgag cgagaccaag      900
tgtaccctga gagccttcac cgtggagaag ggcatctacc agaccagcaa cttcagagtg      960
cagcccaccg agagcatcgt gagattcccc aacatcacca acctgtgccc cttcggcgag     1020
gtgttcaacg ccaccagatt cgccagcgtg tacgcctgga acagaaagag aatcagcaac     1080
tgcgtggccg actacagcgt gctgtacaac agcgccagct tcagcacctt caagtgctac     1140
ggcgtgagcc ccaccaagct gaacgacctg tgcttcacca acgtgtacgc cgacagcttc     1200
gtgatcagag cgacgaggt gagacagatt gcccctggcc agaccggcaa gatcgccgac     1260
tacaactaca agctgcccga cgacttcacc ggctgcgtga tcgcctggaa cagcaacaac     1320
ctggacagca aggtgggcgg caactacaac tacctgtaca gactgttcag aaagagcaac     1380
ctgaagccct tcgagagaga catcagcacc gagatctacc aggccggctc tacccccatgc     1440 aatggcgtgg agggcttcaa ttgctacttc ccccctgcaga gctacggctt ccagcccacc     1500
aacggcgtgg gctaccagcc ctacagagtg gtggtgctga gctttgaact gctgcacgcc     1560
cctgccaccg tgtgcggccc aaagaagagc accaatctgg tgaagaacaa gtgcgtgaac     1620
ttcaacttca cggcctgac cggcaccggc gtgctgaccg agagcaacaa gaagttcctg     1680 ccccttccagc agttcggcag agacatcgcc gacaccaccg atgccgtgag agatccccag     1740
accctggaga tcctggacat caccccctgt agctttggcg gcgtgagcgt gattacccccc     1800 ggcaccaata ccagcaacca ggtggccgtg ctgtaccagg gcgtgaactg caccgaggtg     1860
ccagtggcca tccatgccga ccagctgacc ccaacctgga gagtgtacag caccggcagc     1920
aacgtgttcc agacaagagc cggctgtctg attggcgccg agcacgtgaa taacagctac     1980
gagtgcgata tcccaatcgg cgccggcatc tgtgccagct atcagaccca gaccaatagc     2040
cccagaagag ccagaagcgt ggccagccag agcatcatcg cctacaccat gagcctgggc     2100
gccgagaaca gcgtggccta cagcaacaac agcatcgcca tccccaccaa cttcaccatc     2160
agcgtgacca ccgagatcct gcccgtgagc atgaccaaga ccagcgtgga ctgcaccatg     2220
tacatctgcg gcgacagcac cgagtgcagc aacctgctgc tgcagtacgg cagcttctgc     2280
acccagctga cagagccct gaccggcatc gccgtggagc aggacaagaa cacccaggag     2340
gtgttcgccc aggtgaagca gatctacaag acccccccca tcaaggactt cggcggcttc     2400
aacttcagcc agatcctgcc cgaccccagc aagcccagca agagaagctt catcgaggac     2460
ctgctgttca caaggtgac cctggccgac gccggcttca tcaagcagta cggcgactgc     2520
ctgggcgaca tcgccgccag agacctgatc tgcgcccaga gtttaatgg actgacagtg     2580 ctgccacccc tgctgaccga tgagatgatc gcccagtaca ccagcgctct gctggccggc     2640
acaatcacca gcggctggac atttggagcc ggagccgctc tgcagatccc atttgccatg     2700
cagatggcct acagattcaa cggcatcggc gtgacccaga cgtgctgta cgagaaccag     2760 aagctgatcg ccaaccagtt caacagcgcc atcggcaaga tccaggacag cctgtctagc     2820
acagcctctg ccctgggcaa gctgcaggat gtggtgaacc agaacgccca ggccctgaac     2880
```

-continued

```
accctggtga agcagctgag cagcaacttc ggcgccatca gcagcgtgct gaacgacatc   2940
ctgagcagac tggacccccc tgaggccgag gtgcagatcg acagactgat caccggcaga   3000
ctgcagagcc tgcagaccta cgtgacccag cagctgatca gagccgccga aatcagagcc   3060
agcgccaatc tggccgccac caagatgagc gagtgcgtgc tgggccagag caagagagtg   3120
gacttctgcg gcaagggcta ccacctgatg agctttcccc agagcgcccc tcacggcgtg   3180
gtgtttctgc acgtgaccta cgtgcctgcc caggagaaga acttcaccac cgcccctgcc   3240
atctgccacg atggcaaggc ccacttccct agagagggcg tgttcgtgag caacggcacc   3300
cactggttcg tgacccagag aaacttctac gagccccaga tcatcaccac cgacaacacc   3360
ttcgtgagcg gcaactgcga cgtggtgatc ggcatcgtga acaacaccgt gtacgacccc   3420
ctgcagcccg agctggacag cttcaaggag gagctggaca gtacttcaa gaaccacacc   3480 agccccgatg tggacctggg cgatatcagc ggcatcaatg ccagcgtggt gaacatccag   3540
aaggagatcg accggctcaa tgaggtggcc aagaacctga cgagagcct gatcgacctg   3600 caggaactgg gcaaatatga gcagtacatc aagtggccct ggtacatctg gctgggcttc   3660
atcgccggcc tgatcgccat cgtgatggtg accatcatgc tgtgctgcat gaccagctgc   3720
tgcagctgcc tgaagggctg ctgcagctgc gggtcttgtt gctaa            3765
```

```
<210> SEQ ID NO 13
<211> LENGTH: 1254
<212> TYPE: PRT
<213> ORGANISM: Artificial
<220> FEATURE:
<223> OTHER INFORMATION: An amino acid sequence of modified SARS-CoV-2
      spike protein (SA)

<400> SEQUENCE: 13

Met Phe Val Phe Leu Val Leu Leu Pro Leu Val Ser Ser Gln Cys Val
1               5                   10                  15

Asn Phe Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Ala
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
        130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
```

-continued

```
              195                 200                 205

Pro Ile Asn Leu Val Arg Gly Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Ile Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
                260                 265                 270

Arg Thr Phe Leu Leu Lys Tyr Asn Glu Asn Gly Thr Ile Thr Asp Ala
                275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
                355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Asn Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
    435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Lys Gly Phe Asn Cys Tyr Phe Pro Leu Gln Ser Tyr Gly
                485                 490                 495

Phe Gln Pro Thr Tyr Gly Val Gly Tyr Gln Pro Tyr Arg Val Val Val
                500                 505                 510

Leu Ser Phe Glu Leu Leu His Ala Pro Ala Thr Val Cys Gly Pro Lys
                515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Gly Val Asn Cys Thr Glu Val Pro Val Ala Ile
    610                 615                 620
```

-continued

```
His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                    645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Val Glu Asn Ser
        690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                    725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
        770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                    805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
        850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                    885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                    965                 970                 975

Leu Asn Asp Ile Leu Ser Arg Leu Asp Pro Pro Glu Ala Glu Val Gln
                980                 985                 990

Ile Asp Arg Leu Ile Thr Gly Arg  Leu Gln Ser Leu Gln  Thr Tyr Val
                995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035
```

-continued

```
Arg Val  Asp Phe Cys Gly Lys  Gly Tyr His Leu Met  Ser Phe Pro
    1040             1045              1050

Gln Ser  Ala Pro His Gly Val  Val Phe Leu His Val  Thr Tyr Val
    1055             1060              1065

Pro Ala  Gln Glu Lys Asn Phe  Thr Thr Ala Pro Ala  Ile Cys His
    1070             1075              1080

Asp Gly  Lys Ala His Phe Pro  Arg Glu Gly Val Phe  Val Ser Asn
    1085             1090              1095

Gly Thr  His Trp Phe Val Thr  Gln Arg Asn Phe Tyr  Glu Pro Gln
    1100             1105              1110

Ile Ile  Thr Thr Asp Asn Thr  Phe Val Ser Gly Asn  Cys Asp Val
    1115             1120              1125

Val Ile  Gly Ile Val Asn Asn  Thr Val Tyr Asp Pro  Leu Gln Pro
    1130             1135              1140

Glu Leu  Asp Ser Phe Lys Glu  Glu Leu Asp Lys Tyr  Phe Lys Asn
    1145             1150              1155

His Thr  Ser Pro Asp Val Asp  Leu Gly Asp Ile Ser  Gly Ile Asn
    1160             1165              1170

Ala Ser  Val Val Asn Ile Gln  Lys Glu Ile Asp Arg  Leu Asn Glu
    1175             1180              1185

Val Ala  Lys Asn Leu Asn Glu  Ser Leu Ile Asp Leu  Gln Glu Leu
    1190             1195              1200

Gly Lys  Tyr Glu Gln Tyr Ile  Lys Trp Pro Trp Tyr  Ile Trp Leu
    1205             1210              1215

Gly Phe  Ile Ala Gly Leu Ile  Ala Ile Val Met Val  Thr Ile Met
    1220             1225              1230

Leu Cys  Cys Met Thr Ser Cys  Cys Ser Cys Leu Lys  Gly Cys Cys
    1235             1240              1245

Ser Cys  Gly Ser Cys Cys
    1250
```

```
<210> SEQ ID NO 14
<211> LENGTH: 3765
<212> TYPE: DNA
<213> ORGANISM: Artificial
<220> FEATURE:
<223> OTHER INFORMATION: A nucleotide sequence coding modified
      SARS-CoV-2 spike protein (SA)

<400> SEQUENCE: 14
atgttcgtgt tcctggtgct gctgcccctg gtgagcagcc agtgcgtgaa cttcaccacc      60
agaacccagc tgcccccgc ctacaccaac agcttcacca gaggcgtgta ctaccccgac     120
aaggtgttca gaagcagcgt gctgcacagc acccaggacc tgttcctgcc cttcttcagc     180
aacgtgacct ggttccacgc catccacgtg agcggcacca acggcaccaa gagattcgcc     240
aaccccgtgc tgcccttcaa cgacggcgtg tacttcgcca gcaccgagaa gagcaacatc     300
atcagaggct ggatcttcgg caccaccctg gacagcaaga cccagagcct gctgatcgtg     360
aacaacgcca ccaacgtggt gatcaaggtg tgcgagttcc agttctgcaa cgacccttc     420 ctgggcgtgt actaccacaa gaacaacaag agctggatgg agagcgagtt cagagtgtac     480
agcagcgcca caactgcac cttcgagtac gtgagccagc ccttcctgat ggacctggag     540
ggcaagcagg gcaacttcaa gaacctgaga gagttcgtgt tcaagaacat cgacggctac     600
ttcaagatct acagcaagca caccccatc aacctggtga gaggcctgcc tcagggcttt     660
agcgccctgg agccactggt ggacctgcca atcggcatca acatcaccag attccagacc     720
```

-continued

```
ctgctggccc tgcacatcag ctacctgaca ccaggcgatt ctagctctgg atggacagcc    780
ggcgccgctg cctattacgt gggctacctg cagcctagaa ccttcctgct gaagtacaac    840
gagaacggca ccatcaccga tgccgtggac tgcgccctgg atcccctgag cgagaccaag    900
tgtaccctga gagcttcac cgtggagaag ggcatctacc agaccagcaa cttcagagtg    960
cagcccaccg agagcatcgt gagattcccc aacatcacca acctgtgccc cttcggcgag   1020
gtgttcaacg ccaccagatt cgccagcgtg tacgcctgga acagaaagag aatcagcaac   1080
tgcgtggccg actacagcgt gctgtacaac agcgccagct tcagcacctt caagtgctac   1140
ggcgtgagcc ccaccaagct gaacgacctg tgcttcacca acgtgtacgc cgacagcttc   1200
gtgatcagag cgacgaggt gagacagatt gcccctggcc agaccggcaa catcgccgac   1260
tacaactaca agctgcccga cgacttcacc ggctgcgtga tcgcctggaa cagcaacaac   1320
ctggacagca aggtgggcgg caactacaac tacctgtaca gactgttcag aaagagcaac   1380
ctgaagccct tcgagagaga catcagcacc gagatctacc aggccggctc taccccatgc   1440
aatggcgtga agggcttcaa ttgctacttc cccctgcaga gctacggctt ccagcccacc   1500 tacgcgtgg ctaccagcc ctacagagtg gtggtgctga gctttgaact gctgcacgcc   1560
cctgccaccg tgtgcggccc aaagaagagc accaatctgg tgaagaacaa gtgcgtgaac   1620
ttcaacttca cggcctgac cggcaccggc gtgctgaccg agagcaacaa gaagttcctg   1680
cccttccagc agttcggcag agacatcgcc gacaccaccg atgccgtgag agatccccag   1740
accctggaga tcctggacat cacccctgt agctttggcg gcgtgagcgt gattacccc    1800 ggcaccaata ccagcaacca ggtggccgtg ctgtaccagg gcgtgaactg caccgaggtg   1860
ccagtggcca tccatgccga ccagctgacc ccaacctgga gagtgtacag caccggcagc   1920
aacgtgttcc agacaagagc cggctgtctg attggcgccg agcacgtgaa taacagctac   1980
gagtgcgata tcccaatcgg cgccggcatc tgtgccagct atcagaccca gaccaatagc   2040
cccagaagag ccagaagcgt ggccagccag agcatcatcg cctacaccat gagcctgggc   2100
gtggagaaca gcgtggccta cagcaacaac agcatcgcca tccccaccaa cttcaccatc   2160
agcgtgacca ccgagatcct gcccgtgagc atgaccaaga ccagcgtgga ctgcaccatg   2220
tacatctgcg gcgacagcac cgagtgcagc aacctgctgc tgcagtacgg cagcttctgc   2280
acccagctga cagagccct gaccggcatc gccgtggagc aggacaagaa cacccaggag   2340
gtgttcgccc aggtgaagca gatctacaag accccccca tcaaggactt cggcggcttc   2400
aacttcagcc agatcctgcc cgaccccagc aagcccagca gagaagctt catcgaggac   2460 ctgctgttca caaggtgac cctggccgac gccggcttca tcaagcagta cggcgactgc   2520
ctgggcgaca tcgccgccag agacctgatc tgcgcccaga gtttaatgg actgacagtg   2580 ctgccacccc tgctgaccga tgagatgatc gcccagtaca ccagcgctct gctggccggc   2640
acaatcacca cgcggctggac atttggagcc ggagccgctc tgcagatccc atttgccatg   2700
cagatggcct acagattcaa cggcatcggc gtgacccaga acgtgctgta cgagaaccag   2760
aagctgatcg ccaaccagtt caacagcgcc atcggcaaga tccaggacag cctgtctagc   2820
acagcctctg ccctgggcaa gctgcaggat gtggtgaacc agaacgccca ggccctgaac   2880
accctggtga gcagctgag cagcaacttc ggcgccatca gcagcgtgct gaacgacatc   2940
ctgagcagac tggacccccc tgaggccgag gtgcagatcg acagactgat caccggcaga   3000
ctgcagagcc tgcagaccta cgtgacccag cagctgatca gagccgccga aatcagagcc   3060
```

-continued

```
agcgccaatc tggccgccac caagatgagc gagtgcgtgc tgggccagag caagagagtg      3120
gacttctgcg gcaagggcta ccacctgatg agctttcccc agagcgcccc tcacggcgtg      3180
gtgtttctgc acgtgaccta cgtgcctgcc caggagaaga acttcaccac cgcccctgcc      3240
atctgccacg atggcaaggc ccacttccct agagagggcg tgttcgtgag caacggcacc      3300
cactggttcg tgacccagag aaacttctac gagccccaga tcatcaccac cgacaacacc      3360
ttcgtgagcg gcaactgcga cgtggtgatc ggcatcgtga acaacaccgt gtacgacccc      3420
ctgcagcccg agctggacag cttcaaggag gagctggaca agtacttcaa gaaccacacc      3480
agccccgatg tggacctggg cgatatcagc ggcatcaatg ccagcgtggt gaacatccag      3540
aaggagatcg accggctcaa tgaggtggcc aagaacctga cgagagcct gatcgacctg      3600 caggaactgg gcaaatatga gcagtacatc aagtggccct ggtacatctg gctgggcttc      3660
atcgccggcc tgatcgccat cgtgatggtg accatcatgc tgtgctgcat gaccagctgc      3720
tgcagctgcc tgaagggctg ctgcagctgc gggtcttgtt gctaa                      3765
```

```
<210> SEQ ID NO 15
<211> LENGTH: 1254
<212> TYPE: PRT
<213> ORGANISM: Artificial
<220> FEATURE:
<223> OTHER INFORMATION: An amino acid sequence of modified SARS-CoV-2
      spike protein (BR)

<400> SEQUENCE: 15

Met Phe Val Phe Leu Val Leu Leu Pro Leu Val Ser Ser Gln Cys Val
1               5                   10                  15

Asn Phe Thr Asn Arg Thr Gln Leu Pro Ser Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Tyr Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Ser Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240
```

-continued

```
Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Thr Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Lys Gly Phe Asn Cys Tyr Phe Pro Leu Gln Ser Tyr Gly
                485                 490                 495

Phe Gln Pro Thr Tyr Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Gly Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu Tyr Val
                645                 650                 655
```

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                    725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                    805                 810                 815

Phe Ile Glu Asp Leu Leu Phe Asn Lys Val Thr Leu Ala Asp Ala Gly
                    820                 825                 830

Phe Ile Lys Gln Tyr Gly Asp Cys Leu Gly Asp Ile Ala Ala Arg Asp
                    835                 840                 845

Leu Ile Cys Ala Gln Lys Phe Asn Gly Leu Thr Val Leu Pro Pro Leu
            850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                    885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                    965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
            995                 1000                1005

Thr Gln  Gln Leu Ile Arg Ala  Ala Glu Ile Arg Ala  Ser Ala Asn
    1010                1015                1020

Leu Ala  Ala Tyr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His

-continued

```
        1070              1075              1080

Asp Gly  Lys Ala His Phe Pro  Arg Glu Gly Val Phe  Val Ser Asn
    1085              1090              1095

Gly Thr  His Trp Phe Val Thr  Gln Arg Asn Phe Tyr  Glu Pro Gln
    1100              1105              1110

Ile Ile  Thr Thr Asp Asn Thr  Phe Val Ser Gly Asn  Cys Asp Val
    1115              1120              1125

Val Ile  Gly Ile Val Asn Asn  Thr Val Tyr Asp Pro  Leu Gln Pro
    1130              1135              1140

Glu Leu  Asp Ser Phe Lys Glu  Glu Leu Asp Lys Tyr  Phe Lys Asn
    1145              1150              1155

His Thr  Ser Pro Asp Val Asp  Leu Gly Asp Ile Ser  Gly Ile Asn
    1160              1165              1170

Ala Ser  Phe Val Asn Ile Gln  Lys Glu Ile Asp Arg  Leu Asn Glu
    1175              1180              1185

Val Ala  Lys Asn Leu Asn Glu  Ser Leu Ile Asp Leu  Gln Glu Leu
    1190              1195              1200

Gly Lys  Tyr Glu Gln Tyr Ile  Lys Trp Pro Trp Tyr  Ile Trp Leu
    1205              1210              1215

Gly Phe  Ile Ala Gly Leu Ile  Ala Ile Val Met Val  Thr Ile Met
    1220              1225              1230

Leu Cys  Cys Met Thr Ser Cys  Cys Ser Cys Leu Lys  Gly Cys Cys
    1235              1240              1245

Ser Cys  Gly Ser Cys Cys
    1250
```

```
<210> SEQ ID NO 16
<211> LENGTH: 3765
<212> TYPE: DNA
<213> ORGANISM: Artificial
<220> FEATURE:
<223> OTHER INFORMATION: A nucleotide sequence coding modified
      SARS-CoV-2 spike protein (BR)

<400> SEQUENCE: 16
atgttcgtgt tcctggtgct gctgcccctg gtgagcagcc agtgcgtgaa cttcaccaac    60
agaacccagc tgcccagcgc ctacaccaac agcttcacca gaggcgtgta ctaccccgac   120
aaggtgttca gaagcagcgt gctgcacagc acccaggacc tgttcctgcc cttcttcagc   180
aacgtgacct ggttccacgc catccacgtg agcggcacca cggcaccaa gagattcgac    240 aaccccgtgc tgcccttcaa cgacggcgtg tacttcgcca gcaccgagaa gagcaacatc   300
atcagaggct ggatcttcgg caccaccctg gacagcaaga cccagagcct gctgatcgtg   360
aacaacgcca ccaacgtggt gatcaaggtg tgcgagttcc agttctgcaa ctaccccttc   420
ctgggcgtgt actaccacaa gaacaacaag agctggatgg agagcgagtt cagagtgtac   480
agcagcgcca caactgcac cttcgagtac gtgagccagc ccttcctgat ggacctggag    540
ggcaagcagg gcaacttcaa gaacctgagc gagttcgtgt tcaagaacat cgacggctac   600
ttcaagatct acagcaagca cacccccatc aacctggtga gagacctgcc tcagggcttt   660
agcgccctgg agccactggt ggacctgcca atcggcatca acatcaccag attccagacc   720
ctgctggccc tgcacagaag ctacctgaca ccaggcgatt ctagctctgg atggacagcc   780
ggcgccgctg cctattacgt gggctacctg cagcctagaa ccttcctgct gaagtacaac   840
gagaacggca ccatcaccga tgccgtggac tgcgccctgg atcccctgag cgagaccaag   900
```

-continued

```
tgtaccctga agagcttcac cgtggagaag ggcatctacc agaccagcaa cttcagagtg    960
cagcccaccg agagcatcgt gagattcccc aacatcacca acctgtgccc cttcggcgag   1020
gtgttcaacg ccaccagatt cgccagcgtg tacgcctgga acagaaagag aatcagcaac   1080
tgcgtggccg actacagcgt gctgtacaac agcgccagct tcagcacctt caagtgctac   1140
ggcgtgagcc ccaccaagct gaacgacctg tgcttcacca acgtgtacgc cgacagcttc   1200
gtgatcagag gcgacgaggt gagacagatt gcccctggcc agaccggcac catcgccgac   1260
tacaactaca agctgcccga cgacttcacc ggctgcgtga tcgcctggaa cagcaacaac   1320
ctggacagca aggtgggcgg caactacaac tacctgtaca gactgttcag aaagagcaac   1380
ctgaagccct tcgagagaga catcagcacc gagatctacc aggccggctc taccccatgc   1440
aatggcgtga agggcttcaa ttgctacttc cccctgcaga gctacggctt ccagcccacc   1500
tacggcgtgg gctaccagcc ctacagagtg gtggtgctga gctttgaact gctgcacgcc   1560
cctgccaccg tgtgcggccc aaagaagagc accaatctgg tgaagaacaa gtgcgtgaac   1620
ttcaacttca cggcctgac cggcaccggc gtgctgaccg agagcaacaa gaagttcctg   1680
cccttccagc agttcggcag agacatcgcc gacaccaccg atgccgtgag agatccccag   1740
accctggaga tcctggacat cacccctgt agctttggcg gcgtgagcgt gattacccc   1800 ggcaccaata ccagcaacca ggtggccgtg ctgtaccagg gcgtgaactg caccgaggtg   1860
ccagtggcca tccatgccga ccagctgacc ccaacctgga gagtgtacag caccggcagc   1920
aacgtgttcc agacaagagc cggctgtctg attggcgccg agtacgtgaa taacagctac   1980
gagtgcgata tcccaatcgg cgccggcatc tgtgccagct atcagaccca gaccaatagc   2040
cccagaagag ccagaagcgt ggccagccag agcatcatcg cctacaccat gagcctgggc   2100
gccgagaaca gcgtggccta cagcaacaac agcatcgcca tccccaccaa cttcaccatc   2160
agcgtgacca ccgagatcct gcccgtgagc atgaccaaga ccagcgtgga ctgcaccatg   2220
tacatctgcg gcgacagcac cgagtgcagc aacctgctgc tgcagtacgg cagcttctgc   2280
acccagctga acagagccct gaccggcatc gccgtggagc aggacaagaa cacccaggag   2340
gtgttcgccc aggtgaagca gatctacaag accccccccca tcaaggactt cggcggcttc   2400
aacttcagcc agatcctgcc cgaccccagc aagcccagca agagaagctt catcgaggac   2460
ctgctgttca caaaggtgac cctggccgac gccggcttca tcaagcagta cggcgactgc   2520
ctgggcgaca tcgccgccag agacctgatc tgcgcccaga gtttaatgg actgacagtg   2580 ctgccacccc tgctgaccga tgagatgatc gcccagtaca ccagcgctct gctggccggc   2640
acaatcacca gcggctggac atttggagcc ggagccgctc tgcagatccc atttgccatg   2700
cagatggcct acagattcaa cggcatcggc gtgacccaga cgtgctgta cgagaaccag   2760 aagctgatcg ccaaccagtt caacagcgcc atcggcaaga tccaggacag cctgtctagc   2820
acagcctctg ccctgggcaa gctgcaggat gtggtgaacc agaacgccca ggccctgaac   2880
accctggtga agcagctgag cagcaacttc ggcgccatca gcagcgtgct gaacgacatc   2940
ctgagcagac tggaccccccc tgaggccgag gtgcagatcg acagactgat caccggcaga   3000
ctgcagagcc tgcagaccta cgtgacccag cagctgatca gagccgccga aatcagagcc   3060
agcgccaatc tggccgccat caagatgagc gagtgcgtgc tgggccagag caagagagtg   3120
gacttctgcg gcaagggcta ccacctgatg agctttcccc agagcgcccc tcacggcgtg   3180
gtgtttctgc acgtgaccta cgtgcctgcc caggagaaga acttcaccac cgcccctgcc   3240
atctgccacg atggcaaggc ccacttccct agagagggcg tgttcgtgag caacggcacc   3300
```

-continued

```
cactggttcg tgacccagag aaacttctac gagccccaga tcatcaccac cgacaacacc      3360
ttcgtgagcg gcaactgcga cgtggtgatc ggcatcgtga acaacaccgt gtacgacccc      3420
ctgcagcccg agctggacag cttcaaggag gagctggaca agtacttcaa gaaccacacc      3480
agccccgatg tggacctggg cgatatcagc ggcatcaatg ccagcttcgt gaacatccag      3540
aaggagatcg accggctcaa tgaggtggcc aagaacctga cgagagcct gatcgacctg       3600 caggaactgg gcaaatatga gcagtacatc aagtggccct ggtacatctg ctgggcttc      3660 atcgccggcc tgatcgccat cgtgatggtg accatcatgc tgtgctgcat gaccagctgc      3720
tgcagctgcc tgaagggctg ctgcagctgc gggtcttgtt gctaa                      3765
```

```
<210> SEQ ID NO 17
<211> LENGTH: 1252
<212> TYPE: PRT
<213> ORGANISM: Artificial
<220> FEATURE:
<223> OTHER INFORMATION: An amino acid sequence of modified SARS-CoV-2
      spike protein (IN)

<400> SEQUENCE: 17

Met Phe Val Phe Leu Val Leu Leu Pro Leu Val Ser Ser Gln Cys Val
1               5                   10                  15

Asn Leu Arg Thr Arg Thr Gln Leu Pro Pro Ala Tyr Thr Asn Ser Phe
                20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
        50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Asp Val Tyr
        130                 135                 140

Tyr His Lys Asn Asn Lys Ser Trp Met Glu Ser Gly Val Tyr Ser Ser
145                 150                 155                 160

Ala Asn Asn Cys Thr Phe Glu Tyr Val Ser Gln Pro Phe Leu Met Asp
                165                 170                 175

Leu Glu Gly Lys Gln Gly Asn Phe Lys Asn Leu Arg Glu Phe Val Phe
            180                 185                 190

Lys Asn Ile Asp Gly Tyr Phe Lys Ile Tyr Ser Lys His Thr Pro Ile
        195                 200                 205

Asn Leu Val Arg Asp Leu Pro Gln Gly Phe Ser Ala Leu Glu Pro Leu
        210                 215                 220

Val Asp Leu Pro Ile Gly Ile Asn Ile Thr Arg Phe Gln Thr Leu Leu
225                 230                 235                 240

Ala Leu His Arg Ser Tyr Leu Thr Pro Gly Asp Ser Ser Ser Gly Trp
                245                 250                 255

Thr Ala Gly Ala Ala Ala Tyr Tyr Val Gly Tyr Leu Gln Pro Arg Thr
            260                 265                 270
```

-continued

```
Phe Leu Leu Lys Tyr Asn Glu Asn Gly Thr Ile Thr Asp Ala Val Asp
        275                 280                 285

Cys Ala Leu Asp Pro Leu Ser Glu Thr Lys Cys Thr Leu Lys Ser Phe
    290                 295                 300

Thr Val Glu Lys Gly Ile Tyr Gln Thr Ser Asn Phe Arg Val Gln Pro
305                 310                 315                 320

Thr Glu Ser Ile Val Arg Phe Pro Asn Ile Thr Asn Leu Cys Pro Phe
                325                 330                 335

Gly Glu Val Phe Asn Ala Thr Arg Phe Ala Ser Val Tyr Ala Trp Asn
                340                 345                 350

Arg Lys Arg Ile Ser Asn Cys Val Ala Asp Tyr Ser Val Leu Tyr Asn
        355                 360                 365

Ser Ala Ser Phe Ser Thr Phe Lys Cys Tyr Gly Val Ser Pro Thr Lys
    370                 375                 380

Leu Asn Asp Leu Cys Phe Thr Asn Val Tyr Ala Asp Ser Phe Val Ile
385                 390                 395                 400

Arg Gly Asp Glu Val Arg Gln Ile Ala Pro Gly Gln Thr Gly Lys Ile
                405                 410                 415

Ala Asp Tyr Asn Tyr Lys Leu Pro Asp Asp Phe Thr Gly Cys Val Ile
                420                 425                 430

Ala Trp Asn Ser Asn Asn Leu Asp Ser Lys Val Gly Gly Asn Tyr Asn
        435                 440                 445

Tyr Arg Tyr Arg Leu Phe Arg Lys Ser Asn Leu Lys Pro Phe Glu Arg
    450                 455                 460

Asp Ile Ser Thr Glu Ile Tyr Gln Ala Gly Ser Lys Pro Cys Asn Gly
465                 470                 475                 480

Val Glu Gly Phe Asn Cys Tyr Phe Pro Leu Gln Ser Tyr Gly Phe Gln
                485                 490                 495

Pro Thr Asn Gly Val Gly Tyr Gln Pro Tyr Arg Val Val Val Leu Ser
                500                 505                 510

Phe Glu Leu Leu His Ala Pro Ala Thr Val Cys Gly Pro Lys Lys Ser
        515                 520                 525

Thr Asn Leu Val Lys Asn Lys Cys Val Asn Phe Asn Phe Asn Gly Leu
    530                 535                 540

Thr Gly Thr Gly Val Leu Thr Glu Ser Asn Lys Lys Phe Leu Pro Phe
545                 550                 555                 560

Gln Gln Phe Gly Arg Asp Ile Ala Asp Thr Thr Asp Ala Val Arg Asp
                565                 570                 575

Pro Gln Thr Leu Glu Ile Leu Asp Ile Thr Pro Cys Ser Phe Gly Gly
                580                 585                 590

Val Ser Val Ile Thr Pro Gly Thr Asn Thr Ser Asn Gln Val Ala Val
        595                 600                 605

Leu Tyr Gln Gly Val Asn Cys Thr Glu Val Pro Val Ala Ile His Ala
    610                 615                 620

Asp Gln Leu Thr Pro Thr Trp Arg Val Tyr Ser Thr Gly Ser Asn Val
625                 630                 635                 640

Phe Gln Thr Arg Ala Gly Cys Leu Ile Gly Ala Glu His Val Asn Asn
                645                 650                 655

Ser Tyr Glu Cys Asp Ile Pro Ile Gly Ala Gly Ile Cys Ala Ser Tyr
                660                 665                 670

Gln Thr Gln Thr Asn Ser Arg Arg Ala Arg Ser Val Ala Ser Gln
        675                 680                 685

Ser Ile Ile Ala Tyr Thr Met Ser Leu Gly Ala Glu Asn Ser Val Ala
```

```
           690                 695                 700

Tyr Ser Asn Asn Ser Ile Ala Ile Pro Thr Asn Phe Thr Ile Ser Val
705                 710                 715                 720

Thr Thr Glu Ile Leu Pro Val Ser Met Thr Lys Thr Ser Val Asp Cys
                725                 730                 735

Thr Met Tyr Ile Cys Gly Asp Ser Thr Glu Cys Ser Asn Leu Leu Leu
                740                 745                 750

Gln Tyr Gly Ser Phe Cys Thr Gln Leu Asn Arg Ala Leu Thr Gly Ile
                755                 760                 765

Ala Val Glu Gln Asp Lys Asn Thr Gln Glu Val Phe Ala Gln Val Lys
                770                 775                 780

Gln Ile Tyr Lys Thr Pro Pro Ile Lys Asp Phe Gly Gly Phe Asn Phe
785                 790                 795                 800

Ser Gln Ile Leu Pro Asp Pro Ser Lys Pro Ser Lys Arg Ser Phe Ile
                805                 810                 815

Glu Asp Leu Leu Phe Asn Lys Val Thr Leu Ala Asp Ala Gly Phe Ile
                820                 825                 830

Lys Gln Tyr Gly Asp Cys Leu Gly Asp Ile Ala Ala Arg Asp Leu Ile
                835                 840                 845

Cys Ala Gln Lys Phe Asn Gly Leu Thr Val Leu Pro Pro Leu Leu Thr
        850                 855                 860

Asp Glu Met Ile Ala Gln Tyr Thr Ser Ala Leu Leu Ala Gly Thr Ile
865                 870                 875                 880

Thr Ser Gly Trp Thr Phe Gly Ala Gly Ala Ala Leu Gln Ile Pro Phe
                885                 890                 895

Ala Met Gln Met Ala Tyr Arg Phe Asn Gly Ile Gly Val Thr Gln Asn
                900                 905                 910

Val Leu Tyr Glu Asn Gln Lys Leu Ile Ala Asn Gln Phe Asn Ser Ala
                915                 920                 925

Ile Gly Lys Ile Gln Asp Ser Leu Ser Ser Thr Ala Ser Ala Leu Gly
        930                 935                 940

Lys Leu Gln Asn Val Val Asn Gln Asn Ala Gln Ala Leu Asn Thr Leu
945                 950                 955                 960

Val Lys Gln Leu Ser Ser Asn Phe Gly Ala Ile Ser Ser Val Leu Asn
                965                 970                 975

Asp Ile Leu Ser Arg Leu Asp Pro Pro Glu Ala Glu Val Gln Ile Asp
                980                 985                 990

Arg Leu Ile Thr Gly Arg Leu Gln  Ser Leu Gln Thr Tyr  Val Thr Gln
        995                 1000                1005

Gln Leu  Ile Arg Ala Ala Glu  Ile Arg Ala Ser Ala  Asn Leu Ala
        1010                1015                1020

Ala Thr  Lys Met Ser Glu Cys  Val Leu Gly Gln Ser  Lys Arg Val
        1025                1030                1035

Asp Phe  Cys Gly Lys Gly Tyr  His Leu Met Ser Phe  Pro Gln Ser
        1040                1045                1050

Ala Pro  His Gly Val Val Phe  Leu His Val Thr Tyr  Val Pro Ala
        1055                1060                1065

Gln Glu  Lys Asn Phe Thr Thr  Ala Pro Ala Ile Cys  His Asp Gly
        1070                1075                1080

Lys Ala  His Phe Pro Arg Glu  Gly Val Phe Val Ser  Asn Gly Thr
        1085                1090                1095

His Trp  Phe Val Thr Gln Arg  Asn Phe Tyr Glu Pro  Gln Ile Ile
        1100                1105                1110
```

-continued

```
Thr Thr  Asp Asn Thr Phe Val  Ser Gly Asn Cys Asp  Val Val Ile
    1115                 1120              1125

Gly Ile  Val Asn Asn Thr Val  Tyr Asp Pro Leu Gln  Pro Glu Leu
    1130                 1135              1140

Asp Ser  Phe Lys Glu Glu Leu  Asp Lys Tyr Phe Lys  Asn His Thr
    1145                 1150              1155

Ser Pro  Asp Val Asp Leu Gly  Asp Ile Ser Gly Ile  Asn Ala Ser
    1160                 1165              1170

Val Val  Asn Ile Gln Lys Glu  Ile Asp Arg Leu Asn  Glu Val Ala
    1175                 1180              1185

Lys Asn  Leu Asn Glu Ser Leu  Ile Asp Leu Gln Glu  Leu Gly Lys
    1190                 1195              1200

Tyr Glu  Gln Tyr Ile Lys Trp  Pro Trp Tyr Ile Trp  Leu Gly Phe
    1205                 1210              1215

Ile Ala  Gly Leu Ile Ala Ile  Val Met Val Thr Ile  Met Leu Cys
    1220                 1225              1230

Cys Met  Thr Ser Cys Cys Ser  Cys Leu Lys Gly Cys  Cys Ser Cys
    1235                 1240              1245

Gly Ser  Cys Cys
    1250
```

```
<210> SEQ ID NO 18
<211> LENGTH: 3759
<212> TYPE: DNA
<213> ORGANISM: Artificial
<220> FEATURE:
<223> OTHER INFORMATION: A nucleotide sequence coding modified
      SARS-CoV-2 spike protein (IN)

<400> SEQUENCE: 18
atgttcgtgt tcctggtgct gctgcccctg gtgagcagcc agtgcgtgaa cctgagaacc      60
agaacccagc tgcccccccgc ctacaccaac agcttcacca gaggcgtgta ctaccccgac     120
aaggtgttca gaagcagcgt gctgcacagc acccaggacc tgttcctgcc cttcttcagc     180
aacgtgacct ggttccacgc catccacgtg agcggcacca acggcaccaa gagattcgac     240
aaccccgtgc tgcccttcaa cgacggcgtg tacttcgcca gcaccgagaa gagcaacatc     300
atcagaggct ggatcttcgg caccaccctg gacagcaaga cccagagcct gctgatcgtg     360
aacaacgcca ccaacgtggt gatcaaggtg tgcgagttcc agttctgcaa cgacccctttc     420 ctggacgtgt actaccacaa gaacaacaag agctggatgg agagcggcgt gtacagcagc     480
gccaacaact gcaccttcga gtacgtgagc cagcccttcc tgatggacct ggagggcaag     540
cagggcaact tcaagaacct gagagagttc gtgttcaaga acatcgacgg ctacttcaag     600
atctacagca agcacacccc catcaacctg gtgagagacc tgcctcaggg ctttagcgcc     660
ctggagccac tggtggacct gccaatcggc atcaacatca ccagattcca gaccctgctg     720
gccctgcaca agagctacct gacaccaggc gattctagct ctggatggac agccggcgcc     780
gctgcctatt acgtgggcta cctgcagcct agaaccttcc tgctgaagta caacgagaac     840
ggcaccatca ccgatgccgt ggactgcgcc ctggatcccc tgagcgagac caagtgtacc     900
ctgaagagct tcaccgtgga aaagggcatc taccagacca gcaacttcag agtgcagccc     960
accgagagca tcgtgagatt ccccaacatc accaacctgt gccccttcgg cgaggtgttc    1020
aacgccacca gattcgccag cgtgtacgcc tggaacagaa agagaatcag caactgcgtg    1080
gccgactaca gcgtgctgta caacagcgcc agcttcagca ccttcaagtg ctacggcgtg    1140
```

-continued

```
agccccacca agctgaacga cctgtgcttc accaacgtgt acgccgacag cttcgtgatc   1200
agaggcgacg aggtgagaca gattgcccct ggccagaccg gcaagatcgc cgactacaac   1260
tacaagctgc ccgacgactt caccggctgc gtgatcgcct ggaacagcaa caacctggac   1320
agcaaggtgg gcggcaacta caactacaga tacagactgt tcagaaagag caacctgaag   1380
cccttcgaga gagacatcag caccgagatc taccaggccg gctctaagcc atgcaatggc   1440
gtggagggct tcaattgcta cttccccctg cagagctacg gcttccagcc caccaacggc   1500
gtgggctacc agccctacag agtggtggtg ctgagctttg aactgctgca cgccctgcc   1560 accgtgtgcg gcccaaagaa gagcaccaat ctggtgaaga acaagtgcgt gaacttcaac   1620
ttcaacggcc tgaccggcac cggcgtgctg accgagagca acaagaagtt cctgcccttc   1680
cagcagttcg gcagagacat cgccgacacc accgatgccg tgagagatcc ccagaccctg   1740
gagatcctgg acatcacccc ctgtagcttt ggcggcgtga gcgtgattac ccccggcacc   1800
aataccagca accaggtggc cgtgctgtac cagggcgtga actgcaccga ggtgccagtg   1860
gccatccatg ccgaccagct gaccccaacc tggagagtgt acagcaccgg cagcaacgtg   1920
ttccagacaa gagccggctg tctgattggc gccgagcacg tgaataacag ctacgagtgc   1980
gatatcccaa tcggcgccgg catctgtgcc agctatcaga cccagaccaa tagcagaaga   2040
agagccagaa gcgtggccag ccagagcatc atcgcctaca ccatgagcct gggcgccgag   2100
aacagcgtgg cctacagcaa caacagcatc gccatcccca ccaacttcac catcagcgtg   2160
accaccgaga tcctgcccgt gagcatgacc aagaccagcg tggactgcac catgtacatc   2220
tgcggcgaca gcaccgagtg cagcaacctg ctgctgcagt acggcagctt ctgcacccag   2280
ctgaacagag ccctgaccgg catcgccgtg gagcaggaca agaacaccca ggaggtgttc   2340
gcccaggtga agcagatcta caagacccc cccatcaagg acttcggcgg cttcaacttc   2400
agccagatcc tgcccgaccc cagcaagccc agcaagagaa gcttcatcga ggacctgctg   2460
ttcaacaagg tgaccctggc cgacgccggc ttcatcaagc agtacggcga ctgcctgggc   2520
gacatcgccg ccagagacct gatctgcgcc cagaagtta atggactgac agtgctgcca   2580
cccctgctga ccgatgagat gatcgcccag tacaccagcg ctctgctggc cggcacaatc   2640
accagcggct ggacatttgg agccggagcc gctctgcaga tcccatttgc catgcagatg   2700
gcctacagat tcaacggcat cggcgtgacc cagaacgtgc tgtacgagaa ccagaagctg   2760
atcgccaacc agttcaacag cgccatcggc aagatccagg acagcctgtc tagcacagcc   2820
tctgccctgg gcaagctgca gaacgtggt aaccagaacg cccaggccct gaacaccctg   2880
gtgaagcagc tgagcagcaa cttcggcgcc atcagcagcg tgctgaacga catcctgagc   2940
agactggacc ccctgagggc cgaggtgcag atcgacagac tgatcaccgg cagactgcag   3000
agcctgcaga cctacgtgac ccagcagctg atcagagccg ccgaaatcag agccagcgcc   3060
aatctggccg ccaccaagat gagcgagtgc gtgctgggcc agagcaagag agtggacttc   3120
tgcggcaagg gctaccacct gatgagcttt ccccagagcg cccctcacgg cgtggtgttt   3180
ctgcacgtga cctacgtgcc tgcccaggag aagaacttca ccaccgcccc tgccatctgc   3240
cacgatggca aggcccactt ccctagagag ggcgtgttcg tgagcaacgg cacccactgg   3300
ttcgtgaccc agagaaactt ctacgagccc cagatcatca ccaccgacaa caccttcgtg   3360
agcggcaact gcgacgtggt gatcggcatc gtgaacaaca ccgtgtacga cccccctgcag   3420 cccgagctgg acagcttcaa ggaggagctg gacaagtact tcaagaacca caccagcccc   3480
```

-continued

```
gatgtggacc tgggcgatat cagcggcatc aatgccagcg tggtgaacat ccagaaggag    3540
atcgaccggc tcaatgaggt ggccaagaac ctgaacgaga gcctgatcga cctgcaggaa    3600
ctgggcaaat atgagcagta catcaagtgg ccctggtaca tctggctggg cttcatcgcc    3660
ggcctgatcg ccatcgtgat ggtgaccatc atgctgtgct gcatgaccag ctgctgcagc    3720
tgcctgaagg gctgctgcag ctgcgggtct tgttgctaa                           3759
```

DNA VACCINE FOR SARS-COV-2

TECHNICAL FIELD

The present invention relates to DNA vaccines for inducing immunity against SARS-COV-2 (severe acute respiratory syndrome coronavirus 2) in humans.

BACKGROUND ART

Infectious diseases caused by bacteria and viruses have potential risks of not only localized epidemic but also pandemically spreading. The infectious diseases may become social problems depending on their infectivity and symptoms found in patients. There are many infectious diseases that triggered important historical events, including smallpox, black plague, and influenza (Spanish flu). These infectious diseases have been overcome or their threats have been decreased by development and popularization of chemotherapeutic agents, antibiotics, vaccines, therapeutic agents, etc., and by improvement of sanitary environments. However, risks of newly emerging infectious diseases and re-emerging infectious diseases continue to exist.

Vaccines are effective measures against infectious diseases. Smallpox, which had been feared by people due to its high fatality rate, was eradicated by implementation of an eradication strategy on a global scale. In the eradication process, smallpox vaccines played a very important role. There are some mandatory vaccinations against serious infectious diseases (diphtheria, whooping cough, tetanus, and poliomyelitis in Japan), and they function effectively in maintaining public health.

Naturally occurring or artificially attenuated strains of pathogens, and pathogens inactivated by chemical or physical treatments are known as classical vaccines. For example, influenza vaccines are produced from influenza viruses produced using chicken eggs on a large scale.

In recent years, vaccines containing specific components, for example proteins, of pathogens produced by genetic engineering methods as active ingredients (component vaccines; for example, Patent Literature 1), nucleic acids themselves encoding the proteins (DNA vaccines; for example, Patent Literature 2, and RNA vaccines; for example, Patent Literature 3), and viral vectors carrying the nucleic acids (virus vector vaccines; for example, Patent Literature 4) have been studied.

As mentioned above, techniques for producing vaccines without producing large amounts of pathogens are in the process of being developed. However, for the purpose of creating vaccines with performance sufficient for practical use, it is necessary to design vaccines suitable for target pathogens and their components through trial and error.

CITATION LIST

Patent Literatures

Patent Literature 1: WO2018/074558
Patent Literature 2: WO2014/034735
Patent Literature 3: WO2018/075980
Patent Literature 4: WO2018/189522

SUMMARY OF INVENTION

Problems to be Solved by the Invention

An object of the present invention is to provide a DNA vaccine for the prevention and treatment of SARS-COV-2 infection which is a newly emerging infectious disease.

Solution for the Problems

The present inventors extensively studied the production of a DNA vaccine capable of inducing immunity to SARS-COV-2 with high infectivity in humans. As a result, the present inventors found that the expression efficiency of the spike protein of the virus in cells was remarkably increased by appropriately altering codons in a nucleic acid encoding the spike protein. Thus the present invention was completed.

Specifically, the present invention provides:

[1] a DNA encoding a coronavirus (SARS COV-2) spike protein or a fragment thereof, wherein some or all of contained codons are optimized for expression in a human;

[2] the DNA according to [1], wherein about 50% or more of codons contained in a SARS COV-2 genomic RNA nucleotide sequence encoding the spike protein or a fragment thereof are replaced with other codons;

[3] the DNA according to [1], which encodes the full-length spike protein;

[4] the DNA according to [1], comprising a nucleotide sequence having about 90% or more identity with a nucleotide sequence shown by SEQ ID NO: 3, 12, 14, 16 or 18;

[5] the DNA according to [4], having a nucleotide sequence shown by SEQ ID NO: 3, 12, 14, 16 or 18;

[6] a nucleic acid construct containing a promoter that functions in a human and the DNA according to any one of [1] to [5] operably linked to the promoter;

[7] the nucleic acid construct according to [6], further containing a transcription termination sequence operably linked to the DNA according to any one of [1] to [5];

[8] the nucleic acid construct according to [6] or [7], which is incorporated into a vector;

[9] the nucleic acid construct according to [8], which is incorporated into a vector selected from the group consisting of a plasmid vector, a phage vector and a viral vector;

[10] a pharmaceutical composition comprising the nucleic acid construct according to any one of [6] to [9];

[11] the pharmaceutical composition according to [10], further comprising an adjuvant;

[12] the pharmaceutical composition according to or [11], which is a vaccine for coronavirus infection;

[13] a method for preventing or treating coronavirus infection or alleviating a symptom of coronavirus infection, the method comprising administering the pharmaceutical composition according to [12] to a subject;

[14] the DNA according to [1], which encodes a C-terminal deletion fragment of the spike protein;

[15] the DNA according to [1], which encodes a spike protein or a fragment thereof comprising a K986P and/or V987P mutation, etc.

Effects of the Invention

The present: invention provides a DNA capable of expressing a SARS-COV-2 spike protein with high efficiency in human cells, a nucleic acid construct containing the DNA, and a pharmaceutical composition comprising the nucleic acid construct. The pharmaceutical composition of the present invention is useful for preventing, alleviating symptoms of, or treating SARS-COV-2 viral infection.

MODES FOR CARRYING OUT THE INVENTION

1. DNA of the Present Invention

Figure 1:
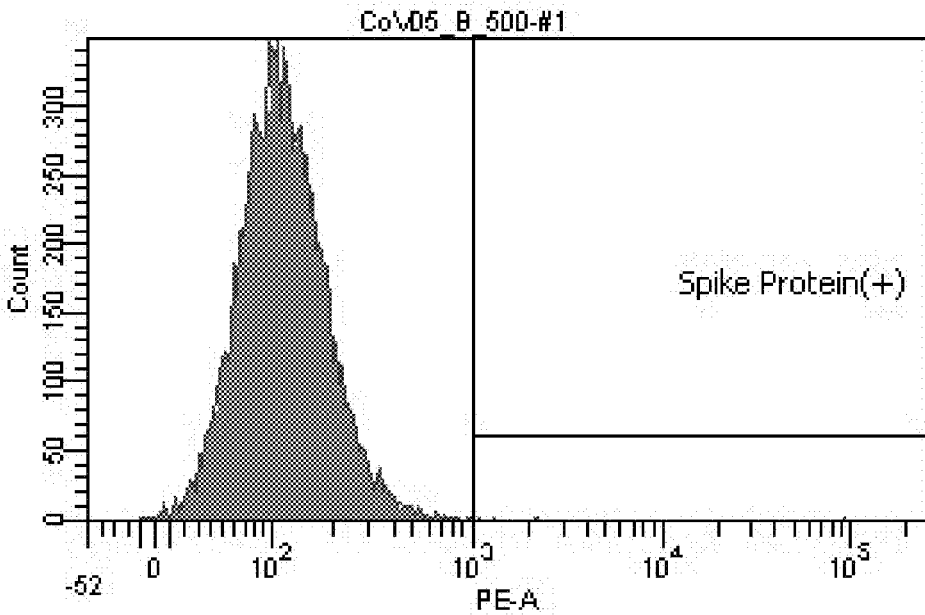
FIG. 1 shows the spike protein expression in control cells.
Figure 2:
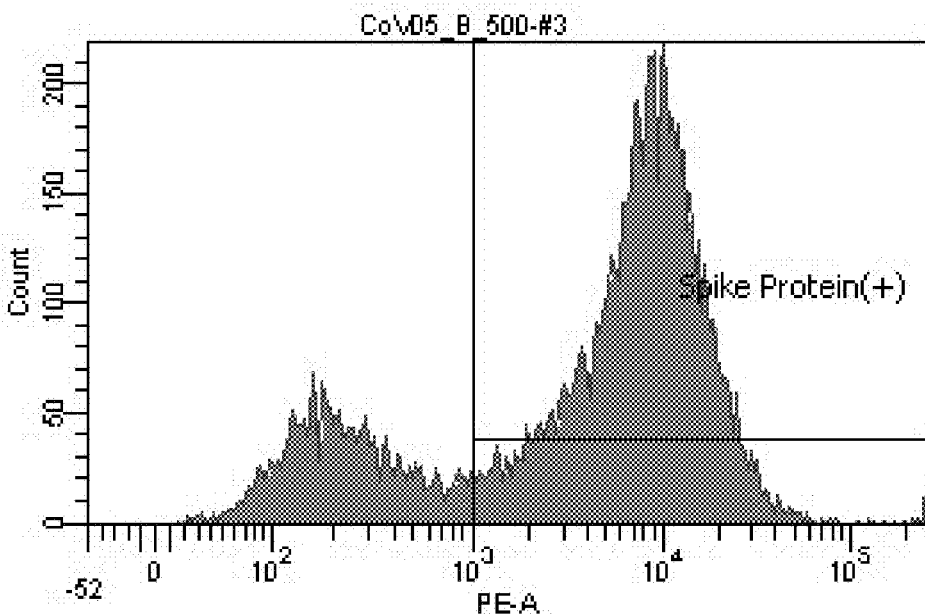
FIG. 2 shows the spike protein expression in cells into which the nucleic acid construct of the present invention was introduced.
Figure 3:
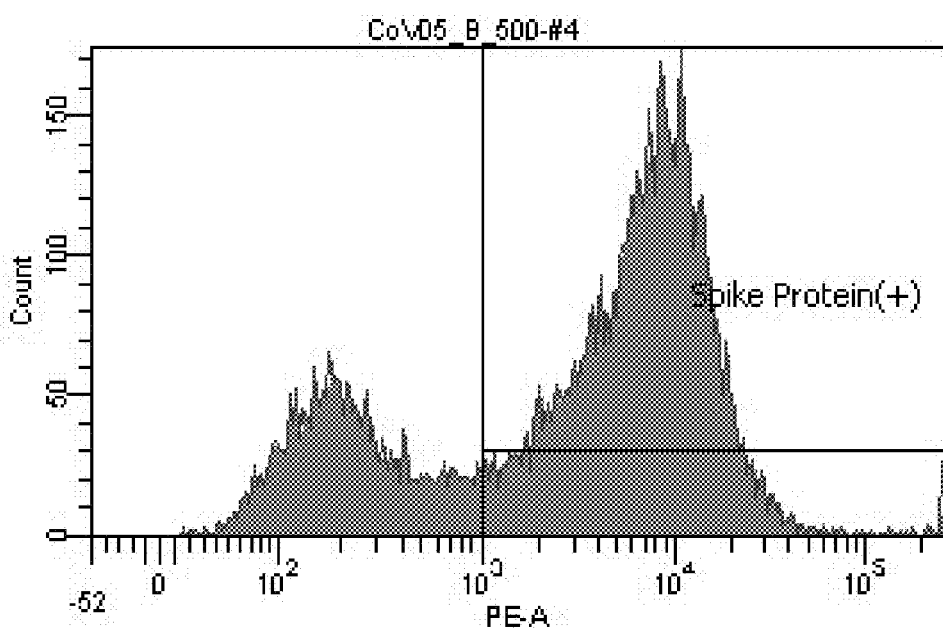
FIG. 3 shows the spike protein expression in cells into which the nucleic acid construct of the present invention was introduced.
Figure 4:
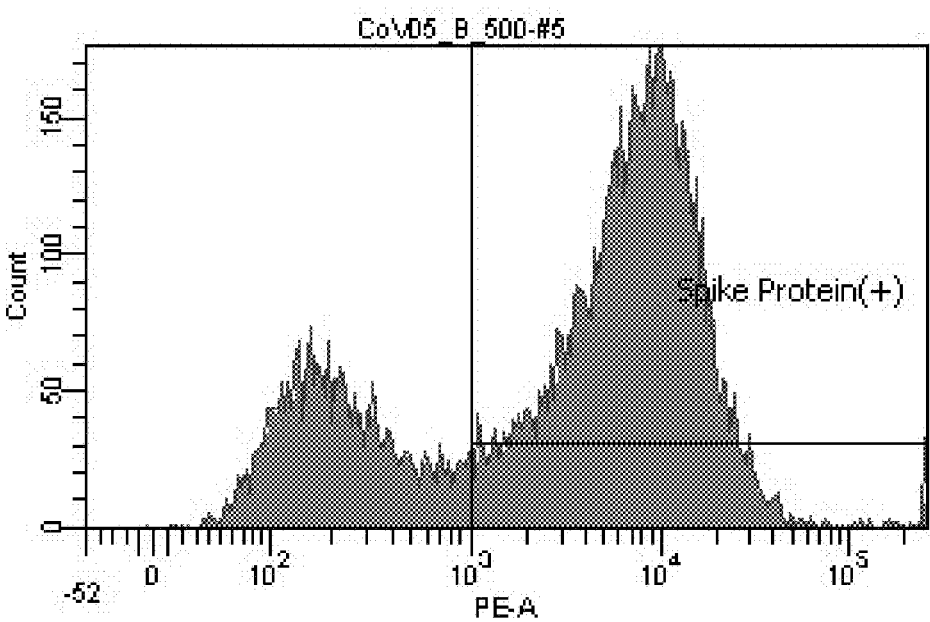
FIG. 4 shows the spike protein expression in cells into which the nucleic acid construct of the present invention was introduced.

The DNA of the present invention is capable of expressing a spike protein of coronavirus (SARS-COV-2) or a fragment thereof in humans, and is used as a DNA vaccine that induces immunity against the virus. Unlike conventional vaccinations comprising administering pathogens themselves or specific components from pathogens to living bodies, DNA vaccines comprise DNAs encoding antigenic proteins of pathogens as essential constituents. Since DNA vaccines can be produced without handling live pathogens, DNA vaccine techniques draw attention in light of the safety and economic efficiency.

The DNA of the present invention is a nucleic acid encoding a SARS-COV-2 spike protein or a fragment thereof, wherein some or all of codons contained in the DNA are optimized for expression in humans, so that the DNA of the present invention can express the spike protein with high efficiency in human bodies. Thus the DNA of the present invention is preferably used for the production of DNA vaccines with high titer.

Coronaviruses are enveloped viruses having positive-strand RNA genomes. Although coronaviruses had been believed to be causative viruses of relatively minor diseases such as head cold, SARS coronavirus (SARS-COV) that was found in 2003 was shown to cause severe respiratory diseases. Spike proteins are present in the coronavirus envelope, and the spike proteins are responsible for receptor binding and cell invasion. The DNA of the present invention can efficiently express the spike protein of SARS-COV-2 (hereinafter sometimes simply referred to as "spike protein") or a fragment thereof in human cells.

The DNA of the present invention may encode the full-length spike protein consisting of about 1300 amino acids, or may encode a fragment consisting of a part of the full-length spike protein. The "fragment" is not particularly limited as long as it has an antigenicity that can induce immunity to SARS-COV-2. For example, the fragment may be about ½ or more, preferably about ⅔ or more, more preferably about ¾ or more, or further preferably about 90% or more the size of the spike protein. The fragment may also be a fragment containing the N-terminus of the full-length spike protein, a fragment containing the C-terminus of the full-length spike protein, or a fragment containing the central region of the full-length spike protein. It is suggested that a fragment comprising deletion of C-terminal 19 amino acids of the SARS-COV spike protein may be expressed in eukaryotic cells at an increased level as compared to a SARS-COV spike protein that does not comprise the above-mentioned deletion (Journal of General Biology, 2005, Vol. 86, p2269-2274). A DNA encoding a SARS-COV-2 spike protein into which the same deletion as described above is introduced can be used in the present invention. A preferred embodiment of the present invention includes a DNA encoding the full-length spike protein.

Information about a SARS-COV-2 isolated in Wuhan is published by GeneBank under accession number NC_045512. As used herein, the amino acid sequence of the SARS-COV-2 spike protein of the Wuhan isolate is referred to as "the wild-type amino acid sequence". The SARS-COV-2 spike protein encoded by the DNA of the present invention may comprise the amino acid sequence of the wild-type spike protein or a fragment thereof, or may comprise an amino acid sequences of a spike protein derived from various coronavirus variants or a fragment thereof. DNAs encoding modified spike proteins, or their fragments, obtained by introducing substitution, deletion (for example, amino acid deletion in a middle region of an amino acid sequence), insertion, and/or addition of at least one amino acid residue, for example one or several amino acid residues into the amino acid sequences as described above are also included in the present invention. As used herein, the term "several" includes, for example, 2 to 15, preferably 2 to 10. For example, a DNA encoding a spike protein comprising a D614G mutation, which was found in a mutant virus isolated from SARS-COV-2-infected patients (Pathogen, 2020, Vol. 9, 324), and a DNA encoding a spike protein comprising K986P/V987P mutations (2P mutations; bioRxiv, Preprint. 2020 Jun. 11), which is known to contribute to high expression of the coronavirus spike protein, can also be used in the present invention. Examples of the modified spike protein include spike proteins comprising amino acid sequences having about 90% or more, preferably about 95% or more, more preferably about 98% identity with an amino acid sequence shown by SEQ ID NO: 1, 11, 13, 15 or 17, or a fragment thereof.

As used herein, codon optimization for expression in humans is achieved, for example, by replacing codons used at low frequency in humans with codons used at high frequency in humans. The codon replacement can be performed with reference to known methods (Nucleic Acids Res., Vol. 30, e43, 2002; WO2004/059556; WO2007/102578, etc.). In addition, information about codon usage frequencies in humans is published (www.kazusa.or.jp). With reference to the information, codons used less frequently in humans, occurring in the wild-type nucleotide sequence encoding SARS-COV-2 spike protein, that is, the nucleotide sequence of the native virus genomic RNA can be replaced with codons more frequently occurring in humans to obtain the nucleotide sequence of the DNA of the present invention. In the nucleotide sequence of the DNA of the present invention, about 50% or more, preferably about 60% or more, more preferably about 70% or more of codons that are contained in a nucleotide sequence encoding the spike protein or a fragment thereof and are present in the SARS-COV-2 genomic RNA are replaced with suitable codons for expression in humans. Thus, when the DNA of the present invention is introduced into human cells, the spike protein can be expressed with high efficiency. One preferred embodiment of the DNA of the present invention is a DNA encoding the full-length spike protein, and an example thereof is a DNA having the nucleotide sequence shown by SEQ ID NO: 3. Another embodiment provides a DNA encoding an amino acid sequence obtained by modification (amino acid substitution, deletion, insertion, or addition) of the amino acid sequence of SEQ ID NO: 1 (for example, a DNA having a nucleotide sequence shown by SEQ ID NO: 12, 14, 16 or 18). Furthermore, examples of preferred embodiments include a DNA comprising a nucleotide sequence having about 90% or more identity, preferably 95% or more identity, more preferably about 98% or more identity, and further preferably about 99% or more identity with the nucleotide sequence of SEQ ID NO: 3, 12, 14, 16 or 18.

The increased efficiency of the expression of spike protein in humans caused by the codon replacement can be confirmed by preparing a nucleic acid construct that contains the DNA of the present invention and is suitable for the spike protein expression in human cells, introducing the construct into human cells, and then evaluating a state of the spike protein expression in the cells. The state of the spike protein expression can be evaluated, for example, by measuring the transcription amount of spike protein mRNA in the cells into which the nucleic acid construct has been introduced or by measuring the amount of spike protein appearing on the cell surface. Examples of a method for measuring the mRNA include a RT-PCR method and a microarray method. Examples of a method for measuring the spike protein include immunological methods using anti-spike protein antibodies. For immunologically measuring the spike protein, a known method, for example, an ELISA method or a method using a cell sorter can be used.

2. Nucleic Acid Construct of the Present Invention

The nucleic acid construct of the present invention is a construct containing the DNA of the present invention and capable of transcribing mRNA corresponding to the spike protein or a fragment thereof from the DNA in cells. Specifically, the nucleic acid construct of the present invention is a nucleic acid construct containing a promoter that functions in humans and the DNA of the present invention located downstream of the promoter.

In the nucleic acid construct of the present invention, the DNA of the present invention is operably linked to a promoter that functions in humans. As used herein, the phrase "operably linked" means that a sequence for controlling gene expression is present in such a position that the sequence can exert its action on a sequence encoding a protein of interest. For example, the phrase "a promoter is operably linked" to a DNA encoding a protein means that the promoter is placed in such a position that transcription can be initiated from the DNA, that is, upstream of the DNA.

The promoter used for the nucleic acid construct of the present invention may be any promoter that can direct RNA transcription from DNA in humans. Examples of the promoter include, but not limited to, promoters derived from mammals (PGK promoter, EF1-alpha promoter, beta-globin promoter, etc.), promoters derived from viruses (CMV promoter, SV40 promoter, MMLV-LTR promoter, HIV-LTR promoter, etc.), and artificially constructed promoters (CAG promoter, etc.). In the present invention, constitutive or inducible promoters can be used. The inducible promoters are usually used in combination with suitable inducers.

In a preferred embodiment, the nucleic acid construct of the present invention contains a transcription termination sequence downstream of the DNA of the present invention. Examples of the transcription termination sequence include poly(A) addition signals that function in humans. Examples of the poly(A) addition signals that can be used for the nucleic acid construct of the present invention include, but not limited to, poly(A) addition signal sequences from SV40 virus, poly(A) addition signal sequences from bovine growth hormone gene, and artificially synthesized poly(A) addition signals. Further, the nucleic acid construct of the present invention may contain an expression control factor other than the control sequences as described above, for example an enhancer sequence. The expression control factor is operably linked to the DNA of the present invention or other factors used in combination. As long as the expression control factor is operably linked to the DNA of the present invention or other factors used in combination, the position of the expression control factor in the nucleic acid construct of the present invention is not particularly limited.

The nucleic acid construct of the present invention may further contain two or more molecules of the DNA of the present invention. In such a case, each of the two or more DNA molecules may be operably linked to separate promoters, or the expression of the spike protein or a fragment thereof from the two or more DNA molecules may be achieved polycistronically by a single promoter. For the polycistronic protein expression, a known element such as an internal ribosome entry site (IRES) or a peptide that is automatically cleaved after translation (P2A peptide, T2A peptide, etc.) can be used. The two or more DNA molecules may be the same molecules, or different molecules (for example, a combination of a DNA encoding the full-length spike protein with a DNA encoding a fragment of the spike protein, a combination of a DNA encoding the wild-type amino acid sequence of the spike protein with a DNA encoding a spike protein having a mutation or a modified spike protein, etc.).

The nucleic acid construct of the present invention can be used in the form of a DNA fragment, for example, the DNA fragment can be administered to a human to express the spike protein therein. The nucleic acid construct of the present invention can be also used in the form of a vector loaded with said nucleic acid construct. Examples of a vector capable of carrying the nucleic acid construct of the present invention include, but not limited to, a plasmid vector, a phage vector, a virus vector, and an artificial chromosome vector. The vector may be appropriately selected depending on intended uses of the nucleic acid construct of the present invention. In the present invention, an available known vector or a newly designed vector can be used. As a promoter or other expression control factors in the nucleic acid construct of the present invention, the promoter or other expression control factors that the vector originally possesses can be utilized. For example, the nucleic acid construct of the present invention can be prepared by ligating the DNA of the present invention to an appropriate position relative to a promoter in an expression vector possessing the promoter. Of course, a promoter or other expression control elements that the vector does not originally possess can be incorporated together with the DNA of the present invention into the vector.

In a case where transient expression of the spike protein in humans is desired, for example, the nucleic acid construct of the present invention may be inserted into a plasmid vector or a virus vector suitable for transient expression (adenovirus vector, adeno-associated virus vector, etc.). In a case where long-term expression of the spike protein is desired, an episomal vector which is replicable in human cells, or a virus vector which has the ability to integrate a loaded gene into a chromosome (retroviral vector, lentiviral vector, etc.) can be utilized.

The vector loaded with the nucleic acid construct of the present invention may contain other elements in addition to the nucleic acid construct. Examples of the other elements include, but not limited to, elements necessary for maintaining vector functions (for example, replication origin, a packaging sequence of a viral vector, etc.). The vector may contain a reporter gene (for example, fluorescent protein gene, enzyme gene, cell surface protein gene, etc.) which indicates that the vector has been introduced into a target cell, or a drug-resistant gene (ampicillin resistant gene, kanamycin resistant gene, etc.) which is useful for eliminating host cells that do not contain a vector in the vector production.

The nucleic acid construct of the present invention can be prepared by a well-known method in the art, depending on its shape. The nucleic acid construct in the form of a nucleic acid fragment can be prepared in large quantities, without using living cells, by a known nucleic acid amplification method, for example PCR or various isothermal nucleic acid amplification methods. The nucleic acid construct loaded on a vector can be prepared by replicating and amplifying the vector in a host compatible with the vector. The nucleic acid construct of the present invention being loaded on a plasmid vector can be prepared by allowing the plasmid to replicate in a host (for example, *E. coli*) in which the vector can replicate, and then extracting and purifying the plasmid from the host cell by a known method to isolate the plasmid. For example, plasmid purification from *E. coli* can be carried out by subjecting a crude plasmid preparation obtained by an alkaline SDS method to a combination of ribonuclease treatment, column chromatography, ultrafiltration and the like. Regarding most of virus vectors used in the field of genetic engineering, preparation methods are well known to those skilled in the art. In addition, many cells suitable for hosts are commercially available. Host cells retaining necessary components for viral vector production (virus-producing cells) can be prepared and then cultured to obtain viral vectors in the cells or in culture supernatants. Thus, the nucleic acid construct of the present invention being loaded on a viral vector can also be prepared without difficulty.

3. Pharmaceutical Composition of the Present Invention

The pharmaceutical composition of the present invention is a composition that can be administered to humans, containing the above-described nucleic acid construct of the present invention. The composition is characterized by containing a pharmaceutically acceptable carrier in addition to the nucleic acid construct of the present invention. The pharmaceutical composition of the present invention may be in any form suitable for the administration route. The pharmaceutical composition of the present invention is usually produced as an injection, a drip, or a parenteral preparation in other forms. Examples of the carrier that may be contained in the parenteral preparation include an aqueous solution for injection, such as a physiological saline and an isotonic solution containing glucose or other adjuvants (D-sorbitol, D-mannitol, sodium chloride, etc.). The pharmaceutical composition of the present invention may further contain, for example, a buffering agent (e.g., phosphate buffer, sodium acetate buffer), an analgesic (e.g., benzalkonium chloride, procaine hydrochloride, etc.), a stabilizer (e.g., human serum albumin, polyethylene glycol, etc.), a preservative, an antioxidant, or the like. Furthermore, the pharmaceutical composition of the present invention may be produced by a freeze-drying method or the like as a solid preparation that can be used by being dissolved in an appropriate aqueous solvent at the time of use.

The pharmaceutical composition of the present invention is representatively used as a DNA vaccine against coronavirus infection. For the purpose of improving the performance as a vaccine, that is, activating an immune response upon administration, the pharmaceutical composition of the present invention may contain an adjuvant as an effective ingredient in addition to the nucleic acid construct of the present invention. Aluminum hydroxide, complete Freund's adjuvant, incomplete Freund's adjuvant, *Bordetella pertussis* adjuvant, etc. are known as classical adjuvants. Further, liposomes, double-stranded RNA poly(I: C), CpG oligonucleotides, etc. are also known to have adjuvant effect.

The pharmaceutical composition of the present invention may contain a component that facilitates cell entry of the nucleic acid construct of the invention. Examples of the component include cationic polymers, cationic lipids, and cationic liposomes, which are known promoters for nucleic acid introduction. The nucleic acid construct of the present invention may be encapsulated in a liposome (including a modified liposome), a virus-like particle (VLP), or an empty AAV capsid particle (e.g., see WO2012/144446). By combining with such a substance, the pharmaceutical composition of the present invention can acquire tropism for specific cells or tissues. For example, when the nucleic acid construct of the present invention is incorporated into a viral vector capable of infecting human cells, the nucleic acid construct of the present invention can be actively taken up by cells capable of being infected by the viral vector.

When the pharmaceutical composition of the present invention is administered to a human, the spike protein or a fragment thereof expressed from the nucleic acid construct of the present invention is recognized as an antigen in the human body. As a result, immunity to SARS-COV-2 is induced in the human, and then, prevention of infection with the virus and/or alleviation of symptoms of the virus infection is achieved. A dose and administration frequency of the pharmaceutical composition of the present invention are not particularly limited, and may be appropriately adjusted according to the effect exerted. An administration route of the pharmaceutical composition of the present invention is not particularly limited, and however, from the viewpoint of exerting the effect, it is preferable that the pharmaceutical composition of the present invention is parenterally administered. The pharmaceutical composition of the present invention is usually administered in a tissue (for example, intramuscularly), intravenously, intracutaneously, subcutaneously, intraperitoneally, or the like, by injection, drip, or other means.

Hereinafter, the present invention is explained in more detail with reference to Examples to which the present invention is not limited.

EXAMPLES

Example 1. Preparation of DNA Encoding Sars-Cov-2 Spike Protein

Information about the gene of the SARS-COV-2 Wuhan strain has been published in GeneBank under accession number NC_045512. Information about an amino acid sequence of SARS-CoV-2 spike protein (SEQ ID NO: 1) and a nucleotide sequence (SEQ ID NO: 2) encoding the amino acid sequence can be obtained from the GeneBank. A DNA having a sequence (SEQ ID NO: 2) corresponding to the nucleotide sequence of the viral genomic RNA encoding the spike protein was chemically synthesized. At this time, a recognition sequence for restriction enzyme NheI was added on the 5' side of the start codon of SEQ ID NO: 2, together with four bases of 5'-CACC-3' intervening between the recognition sequence and the start codon. A recognition sequence for restriction enzyme XbaI was added on the 3' side of the stop codon (TAA) and adjacent to the stop codon.

Next, a DNA was designed to change codons within the open reading frame of the SARS-COV-2 spike protein in SEQ ID NO: 2 into codons suitable for expression in humans. Of a total of 1273 codons excluding the stop codon, 967 codons were converted into other codons without amino acid substitution to obtain a nucleotide sequence shown by SEQ ID NO: 3. Then, a DNA having the nucleotide sequence was chemically synthesized. On the 5' side of the start codon of the DNA thus obtained, a recognition sequence for restriction enzyme NheI was added together with four bases of 5'-CACC-3' intervening between the recognition sequence and the start codon. On the 3' side of the stop codon (TAA) of the DNA, a recognition sequence for restriction enzyme XbaI was added adjacent to the stop codon. The sequence 5'-CACC-3' forms a Kozak sequence together with two bases (GC) in the immediately preceding NheI recognition sequence.

Example 2. Preparation of Spike Protein Expression Plasmid

Each of the DNA comprising the nucleotide sequence of SEQ ID NO: 2 and the DNA comprising the nucleotide sequence of SEQ ID NO: 3 as prepared in Example 1 was digested with two restriction enzymes NheI and XbaI (both manufactured by Takara Bio Inc.). The resulting DNA fragment was inserted between NheI and XbaI sites in plasmid vector pVAX1 (manufactured by Thermo Fisher Scientific) to prepare recombinant plasmids. A plasmid containing the SARS-COV-2 spike protein open reading frame connected in such a direction that transcription from a cytomegalovirus (CMV) promoter of pVAX1 and translation were allowed was selected. Such a plasmid containing the DNA comprising the nucleotide sequence of SEQ ID NO: 2 was named "plasmid WT". Such a plasmid containing the DNA comprising the nucleotide sequence of SEQ ID NO: 3 was named "plasmid CO". These plasmids contain a T7 promoter, which is an element originally loaded on pVAX1, on the 5' side of the open reading frame (downstream of the CMV promoter), and a bovine growth hormone factor gene-derived polyadenylation sequence on the 3' side of the open reading frame. The entire nucleotide sequence of plasmid CO is shown by SEQ ID NO: 4.

*Escherichia coli* HST08 strain (manufactured by Takara Bio Inc.) was transformed with plasmid WT or plasmid CO, and then cultured in a liquid medium containing kanamycin. From *E. coli* cells thus obtained, the plasmids were purified using NucleoBond XtraMidi (manufactured by Macherey-Nagel), and then used in experiments as described below.

Example 3. Preparation of Primer for mRNA Quantification

A pair of primers was prepared for quantifying the mRNA of SARS-COV-2 spike protein transcribed in cells into which plasmid WT or plasmid CO was introduced. For the mRNA transcribed from plasmid WT, a pair of CoV-S1-WT-Q1_F (SEQ ID NO: 5) and CoV-S1-WT-Q1_R (SEQ ID NO: 6) (hereinafter referred to as primer pair WT-1) was synthesized. For the mRNA transcribed from plasmid CO, a pair of CoV-S1-CO-Q3_F (SEQ ID NO: 7) and CoV-S1-CO-Q3_R (SEQ ID NO: 8) (hereinafter referred to as primer pair CO-3) was synthesized. Further, for quantifying the mRNA of human GAPDH gene as an internal standard, a pair of primers GAPDH_F (SEQ ID NO: 9) and GAPDH_R (SEQ ID NO: 10) (hereinafter referred to as primer pair GAPDH) was synthesized.

Example 4. Confirmation of mRNA Transcription from Recombinant Plasmid

Into wells of a cell culture plate containing DMEM containing 10% fetal bovine serum (FBS) and 1% penicillin-streptomycin, $1.6 \times 10^5$ HEK293T cells were added. The cells were then transfected with 300 ng of plasmid WT, plasmid CO, or pVAX1 using TransIt-293 (manufactured by Mirus). Further, a cell (mock) that was not transfected with any plasmid was prepared. These cells were cultured at 37° C. and in 5% $CO_2$.

From the cells cultured for two days, RNA was purified using NucleoSpin RNA Plus (manufactured by Macherey-Nagel). Then, the RNA was subjected to RT-PCR using the primer pairs prepared in Example 3 to quantify the mRNA of SARS-COV-2 spike protein transcribed in the cells. For RT-PCR, PrimeScript RT Master Mix (manufactured by TAKARA BIO INC.) and TB Green Premix Ex Taq II (Tli RNaseH Plus) (manufactured by TAKARA BIO INC.) were used according to instructions attached thereto. Table 1 shows Ct values measured in combinations of RNAs from the cells and the primer sets.

As shown in Table 1, significant amounts of the spike protein mRNA were detected only with the combination of plasmid WT and primer pair WT-1 and the combination of plasmid CO and primer pair CO-3. Further, when mRNA transcription levels in the cell transfected with plasmid WT and the cell transfected with plasmid CO were compared by a ΔΔCt method, the mRNA transcription level in the cell transfected with plasmid CO was 46 times higher than the mRNA transcription level in the cell transfected with plasmid WT.

TABLE 1

| | Primer pair | | |
|---|---|---|---|
| Plasmid | WT-1 | CO-3 | GAPDH |
| pVAX1 | 34.285 | Not detected | 17.215 |
| WT | 19.165 | 37.41 | 17.015 |
| CO | 32.72 | 13.84 | 17.22 |
| mock | 34.5 | Not detected | 16.82 |

Example 5. Confirmation of Spike Protein Expression (1)

HEK293T cells transfected with plasmid WT, plasmid CO, or pVAX1 were prepared in the same manner as in Example 4. Two groups of the cells transfected with plasmid WT were prepared. The cells cultured for two days were analyzed by a flow cytometer (BD FACS Canto II; manufactured by BD Biosciences) to calculate a positive rate for the SARS-CoV-2 spike protein. The spike protein was detected by using a mouse anti-spike monoclonal antibody (Anti-SARS-COV-2 Spike, Mouse-Mono (1A9); manufactured by GeneTex) and a PE-labeled anti-mouse IgG antibody (Mouse Immunoglobulins/RPE; manufactured by Agilent) in combination.

Table 2 shows a proportion of spike protein-positive cells in each cell group. In the cell group transfected with plasmid WT, the proportion of spike protein-positive cells was similar to the background (the proportion of spike protein-positive cells in the pVAX1-introduced cell group). In the cell group transfected with plasmid CO, the expression of the spike protein was confirmed in more than 40% of the cells.

TABLE 2

| Plasmid | Positive rate |
|---------|---------------|
| pVAX1   | 0.2%          |
| WT (1)  | 0.1%          |
| WT (2)  | 0.2%          |
| CO      | 40.6%         |

Example 6. Confirmation of Spike Protein Expression (2)

Using the plasmid CO prepared in Example 2 and three lots of newly prepared plasmid CO (referred to as <1>, <2> and <3>, respectively), their ability to allow the spike protein to express was verified in HEK293T cells.

The preparation of cells and the measurement of spike protein expression were carried out in the same manner as in Example 5 except that transfection was carried out under two conditions: condition A (200 ng of plasmid was added to $1.6 \times 10^5$ of HEK293T cells) and condition B (500 ng of plasmid was added to $0.8 \times 10^5$ of HEK293T cells). Table 3 shows a proportion of spike protein-positive cells and a mean fluorescence intensity of PE in each cell group. Further, histograms showing spike protein expression levels in cells transfected with pVAX1, plasmid CO <1>, <2> and <3> under condition B are shown in FIGS. 1 to 4, respectively. As is clear from these results, plasmid CO stably induced the spike protein expression in the cells into which the plasmid was introduced, regardless of production lots. Both the spike protein expression-positive rate and the mean PE fluorescence intensity were correlated with the amount of plasmid used.

TABLE 3

|         | Condition A | | Condition B | |
|---------|------------------|-----------------------------------|------------------|-----------------------------------|
| Plasmid | Positive rate | Mean fluorescent intensity | Positive rate | Mean fluorescent intensity |
| pVAX1   | 0.1%  | —    | 0.1%  | —          |
| CO (Example 2) | 44.8% | 8051 | Not tested | Not tested |
| CO<1>   | 37.7% | 7670 | 77.5% | 10979      |
| CO<2>   | 36.5% | 7411 | 72.8% | 10792      |
| CO<3>   | 39.7% | 7426 | 73.8% | 11157      |

Example 7. Confirmation of Immunity Induction by Recombinant Plasmid (1)

Using the plasmid CO prepared in Example 2, the ability to induce immunity with or without an adjuvant was evaluated.

In two groups of six SD rats (purchased from Clea Japan, Inc.) each, 666.6 μg/400 μL per rat of plasmid CO, or a combination of 666.6 μg/200 μL per rat of plasmid CO and 200 μL per rat of ALUM adjuvant (manufactured by InVivoGen) was administered to the tibialis anterior muscles (left and right) of the rats. The rats were reared in an environment where the rats could ingest feed and water ad libitum. As a control group, three rats were reared without any treatment under the same conditions. Two weeks after administration, blood was collected from the tail vein of the rats and sera were prepared. Anti-spike protein antibodies in the sera were measured by a method as described below.

A 96-well plate coated with Recombinant 2019-nCOV Spike S1+S2 Protein (ECD, His tag; manufactured by Beta Life Sciences) was blocked using a blocking solution [PBS-T containing 5% skimmed milk (PBS-T: a phosphate-buffered saline containing 0.05% Tween 20)]. Then, the serum diluted 8-fold with the blocking solution was added to the plate. The plate was left to stand overnight at 4° C. The next day, the wells were washed, and an HRP (horse radish peroxidase)-labeled anti-rat antibody (GH Healthcare) was added. Then, the plate was left to stand at room temperature for 3 hours. After the wells were washed with PBS-T, 3,3'-5,5'-tetramethylbenzidine (manufactured by Sigma-Aldrich) was added to the wells. After the plate was left to stand at room temperature for 30 minutes, 0.5N sulfuric acid was added to the wells to stop a chromogenic reaction. Absorbance at 450 nm was measured for each well to evaluate the anti-spike protein antibodies in the serum.

Figure 5:
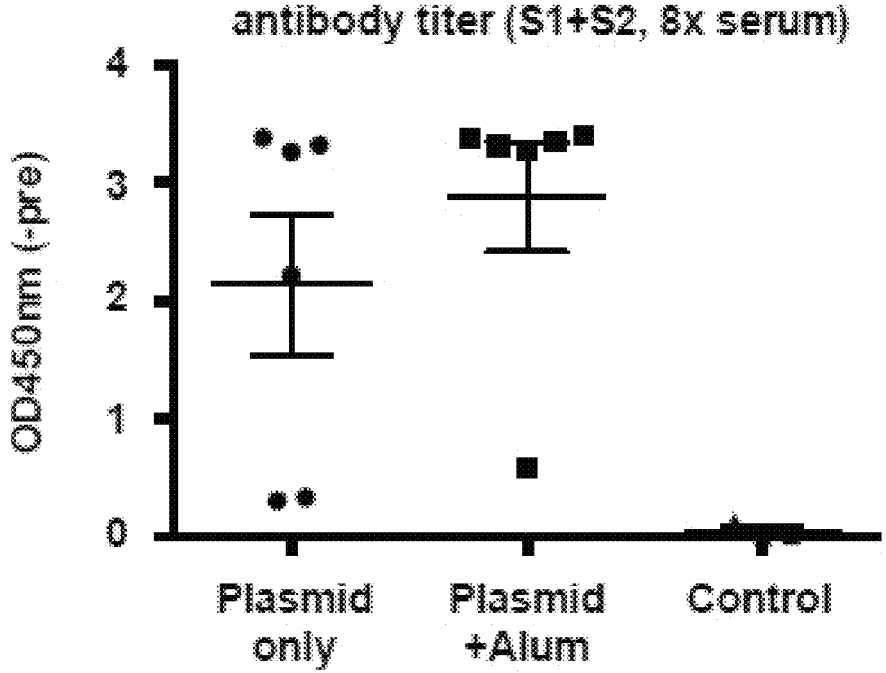
FIG. 5 shows the production of anti-spike protein antibodies in rats to which the nucleic acid construct of the present invention was administered.

Results are shown in FIG. 5. In the plasmid CO-administered groups, the antibodies that bound to the spike protein were produced regardless of the presence or absence of the ALUM adjuvant. However, in the adjuvant-administered group, higher antibody titer tended to be observed.

Example 8. Confirmation of Immunity Induction by Recombinant Plasmid (2)

To six SD rats, 666.6 μg per rat of plasmid CO and 66.7 μl per rat of ALUM adjuvant were administered. The administration was carried out 3 times at intervals of 2 weeks. At the 4th week, 6th week and 8th week from the start of administration, blood was collected, and the amount of anti-spike protein antibodies in sera was measured. The antibody measurement was performed in the same manner as in Example 7 except that a test using Recombinant 2019-nCOV Spike protein (RBD; manufactured by Beta Life Sciences) as an antigen was added. As a result, it was found that both antibodies that bound to S1+S2 and antibodies that bound to RBD (receptor binding domain) were produced in the rats. The both antibodies were already detected in the sera at the 4th week from the start of administration, and an increase in antibody titer was observed from the 4th week to the 8th week.

Furthermore, the same measurement was performed on a plate coated with Recombinant 2019-nCOV Spike (S1-D614G; manufactured by Sino Biological), and as a result, it was found that the antibodies produced by plasmid CO recognized the spike protein comprising D614G mutation.

Example 9. Confirmation of Cell-Mediated Immunity Induction

Effect of plasmid CO on cell-mediated immunity was investigated using T cell ELISPOT Kits (INF-γ and IL-4; manufactured by U-CyTech Bioscience) according to instructions attached to the kit.

A 96-well plate equipped with a PVDF membrane on its bottom (manufactured by Millipore) was coated with an anti-IFNγ capture antibody or an anti-IL4 capture antibody attached to the kit. The Plate was washed with the blocking solution. Into wells of the plate, 3×10⁵ spleen cells prepared from rats immunized with plasmid co by a conventional method were seeded together with Recombinant 2019-nCOV Spike S1+S2 Protein or Recombinant 2019-nCOV Spike protein (RBD). The plate was incubated at 37° C. for 48 hours. After the incubation, the wells were washed with PBS-T, and a biotinylated anti-rat IFNγ antibody or a biotinylated anti-rat IL4 antibody was added. The plate was left at 4° C. for 2 hours. Then, HRP-labeled streptavidin was added to the wells and the plate was left to stand for 1 hour. An HRP substrate solution was added to the wells to detect HRP activity. As a result, stimulation with S1+S2 or stimulation with RBD markedly increased interferon-γ (INFγ) production from the spleen cells of immunized rats, and slightly increased production of nterleukin-4 (IL4) from the spleen cells of immunized rats. From these results, it was found that plasmid CO induces Th1-type cell-mediated immunity.

Example 10. Evaluation of Toxicity

Lung, liver, kidney and heart tissues were collected from rats 7 weeks after immunization with plasmid CO, and HE-stained tissue sections were prepared. As a result of observation under a microscope, no findings of toxicity were observed. When various biochemical markers in sera from the rats were measured, no values deviating from normal ranges were obtained.

Example 11. Preparation of Plasmid Loaded with DNA Encoding Modified Spike Protein Regarding various SARS-COV-2 variants reported by the World Health Organization (WHO), amino acid sequences of their spike proteins were investigated. Among these, B. 1.1.7 variant, B.1.351 variant, P.1 variant, B.1.617.2 variant (labeled with Alpha, Beta, Gamma, and Delta, respectively by the WHO) were selected, and four amino acid sequences were designed to introduce some of mutations that had been found in the variants into the amino acid sequence of the wild-type spike protein (SEQ ID NO: 1). The four amino acid sequences (named 4GP, SA, BR, and IN, respectively) comprise the mutation(s) derived from the respective variants, and K986P/V987P mutations and deletion of C-terminal 19 amino acids which were known to contribute to high expression of spike protein. Then, DNA nucleotide sequences encoding these amino acid sequences and suitable for expression in humans were designed.

Table 4 shows information about the newly designed amino acid sequences, SEQ ID: NOs of the amino acid sequences, and SEQ ID: NOs of the DNA nucleotide sequences encoding the amino acid sequences. In Table 4, amino acid positions are based on the amino acid sequence shown by SEQ ID NO: 1. As compared with the genomic RNA sequence encoding the wild-type SARS-COV-2 spike protein, 70% or more of codons in the DNA nucleotide sequences excluding parts encoding the modifications are replaced by codons suitable for expression in humans.

TABLE 4

| | | SEQ ID NO. | |
| Name | Modifications introduced into SEQ ID NO: 1 | Amino acid sequence | DNA nucleotide sequence |
| --- | --- | --- | --- |
| 4GP | Amino acid substitution: D614G, K986P, and V987P Deletion: C-terminal 19 amino acids | 11 | 12 |
| SA | Amino acid substitution: L18F, D80A, D215G, R246I, K417N, E484K, N501Y, D614G, A701V, K986P, and 987P Deletion: C-terminal 19 amino acids | 13 | 14 |
| BR | Amino acid substitution: L18F, T20N, P26S, D138Y, R190S, K417T, E484K, N501Y, D614G, H655Y, K986P, V987P, T1027I, and V1176F Deletion: C-terminal 19 amino acids | 15 | 16 |
| IN | Amino acid substitution: T19R, G142D, E156G, L452R, T478K, D614G, P681R, D950N, K986P, and V987P Deletion: F157, R158, and C-terminal 19 amino acids | 17 | 18 |

DNAs of nucleotide sequences of SEQ ID NOS: 12, 14, 16 and 18 were chemically synthesized. Then, the open reading frame region of the SARS-COV-2 spike protein contained in the plasmid CO was replaced by these DNAs to prepare plasmids capable of expressing the modified spike proteins. The plasmids thus obtained were named plasmid 4GP, plasmid SA, plasmid BR, and plasmid IN, respectively. *Escherichia coli* HST08 strain was transformed with each plasmid and cultured in a liquid medium containing kanamycin. From the *E. coli* cells thus obtained, the plasmids were purified using NucleoBond XtraMidi (manufactured by Macherey-Nagel), and used in experiments as described below.

Example 12. Confirmation of Modified Spike Protein Expression

HEK293T cells were transfected with plasmid CO, or plasmids 4GP, SA, BR or IN and cultured in the same manner as in Example 4. The cells cultured for two days were analyzed by a flow cytometer (BD FACS Canto II) to evaluate the SARS-COV-2 spike protein expression (4 groups each). For detection of the spike protein, an anti-S1 antibody: SARS-CoV-2 (2019-nCOV) Spike S1 Antibody (Rabbit Mab; manufactured by Sino Biological), and an anti-S2 antibody: Anti-SARS-COV-2 Spike, Mouse-Mono (1A9) were used in combination with an anti-rabbit secondary antibody and an anti-mouse secondary antibody (the both antibodies were fluorescently labeled), respectively.

Figure 6:
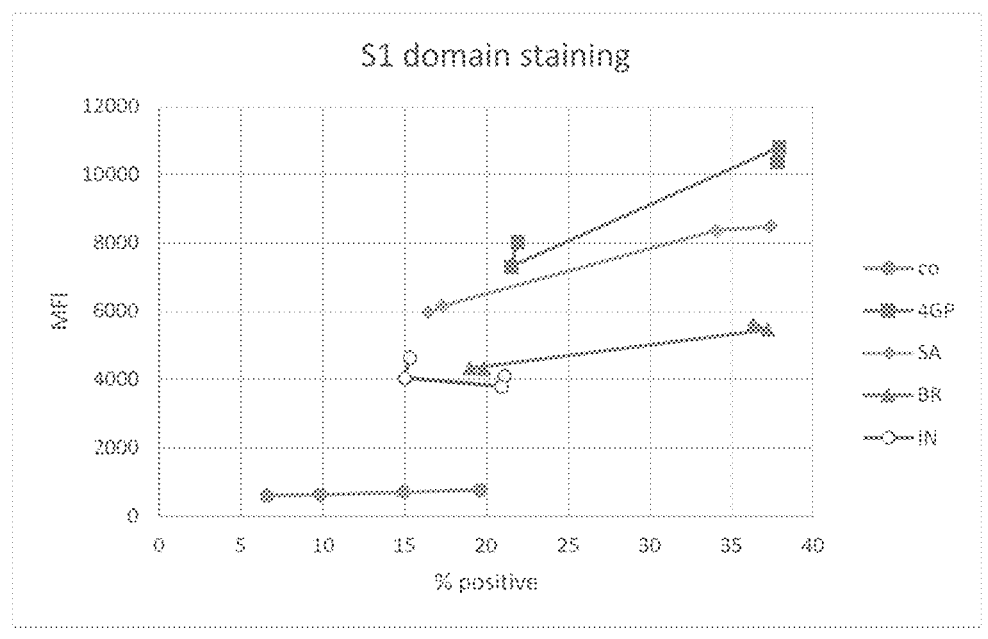
FIG. 6 shows spike protein positive rates and fluorescence intensities in cells into which the nucleic acid construct of the present invention was introduced.
Figure 7:
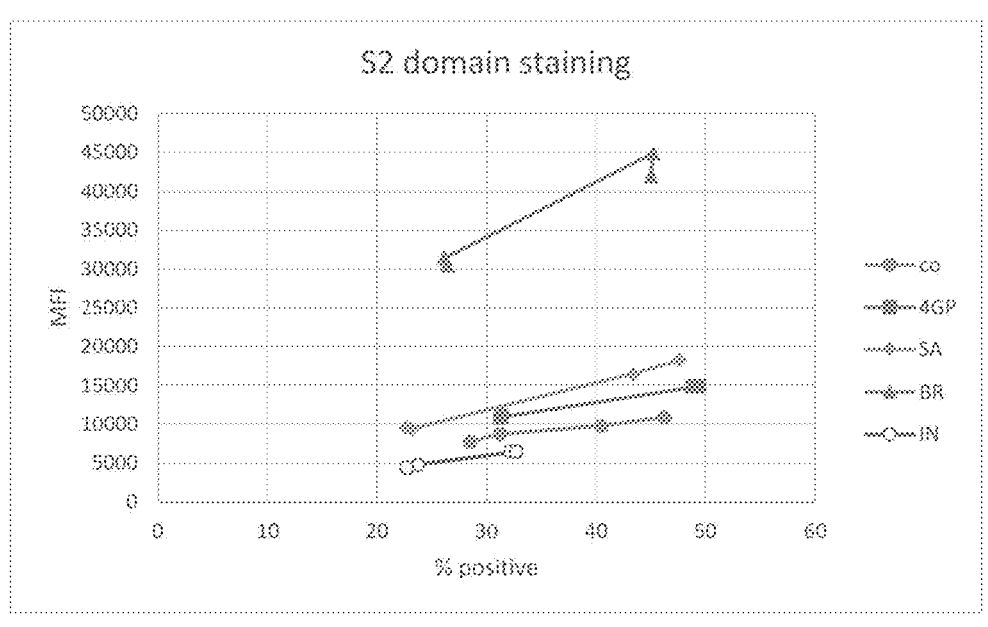
FIG. 7 shows spike protein positive rates and fluorescence intensities in cells into which the nucleic acid construct of the present invention was introduced.

Spike protein-positive cells in the cell groups transfected with each plasmid were analyzed using the anti-S1 antibody and the anti-S2 antibody. Results are shown in FIG. 6 and FIG. 7. In the Figures, horizontal axes indicate proportions of spike protein-positive cells in the total cells, vertical axes indicate mean fluorescence intensities of fluorescence derived from the label measured in the tests, and CO, 4GP, SA, BR and IN indicate plasmids CO, 4GP, SA, BR and IN-introduced cell groups, respectively. As shown in FIGS. 6 and 7, though the results varied between detection with the anti-S1 antibody and detection with the anti-S2 antibody, overall, the spike protein expression levels in the cells transfected with plasmids 4GP, SA, BR, and IN did not appear to be lower than the spike protein expression levels in the cells transfected with plasmid CO.

Example 13. Confirmation of Immunity Induction by Modified Spike Protein

Using plasmid 4GP, immunity induction was evaluated by the method described in Example 7. In a plasmid 4GP-administered rat group, the production amount of anti-spike protein antibodies two weeks after the administration was higher than that in a plasmid CO-administered rat group. When the rats were continuously reared and the antibody production in the rats was investigated, the difference in the antibody production amount between the two plasmid-administered groups was no longer observed. This was probably because of the saturation of the production amount.

Example 14. Analysis of Antibody Produced by Modified Spike Protein

Using plasmid CO and plasmid SA, the ability to induce immunity was evaluated. Three groups of three to eight SD rats (purchased from CLEA Japan, Inc.) each were prepared. A mixture of 666.6 μg/333.3 μL of pVAX (control), plasmid CO or plasmid SA, and 66.7 μL of ALUM adjuvant (manufactured by InVivogen) was prepared, and 400 μL per rat of the mixture was administered to the rats (200 μL of the mixture was administered each to the left and right tibialis anterior muscles). The rats were reared in an environment where the rats could ingest feed and water ad libitum. As a no-treatment group, rats three were reared without administrating any plasmid under the same conditions. Two weeks after administration, blood was collected from the tail vein of the rats and sera were prepared. Anti-spike protein antibodies in the sera were measured by a method as described below.

Antibody titers against various SARS-COV-2 spike proteins of antibodies contained in the sera in the four groups were measured. Spike proteins having amino acid sequences derived from Wuhan, Alpha, Beta, and Gamma strains (with His-Tag; all manufactured by ACRO Biosystems) were used as spike proteins. A 96-well plate coated with the spike protein was blocked with a blocking solution [PBS-T containing 5% skimmed milk]. Then, the serum diluted serially from 50-fold with the blocking solution was added to wells, and the plate was left to stand at 4° C. overnight. Next day, the wells were washed, an HRP-labeled anti-rat antibody (GH Healthcare) was added to the wells, and the plate was left to stand at room temperature for 3 hours. After washing the wells with PBS-T, 3,3'-5,5'-tetramethylbenzidine (manufactured by Sigma-Aldrich) was added to the wells. After the plate was left to stand at room temperature for 30 minutes, 0.5N sulfuric acid was added to the wells to stop a chromogenic reaction. Absorbance at 450 nm was measured for each well to evaluate the anti-spike protein antibodies in the serum.

Figure 8:
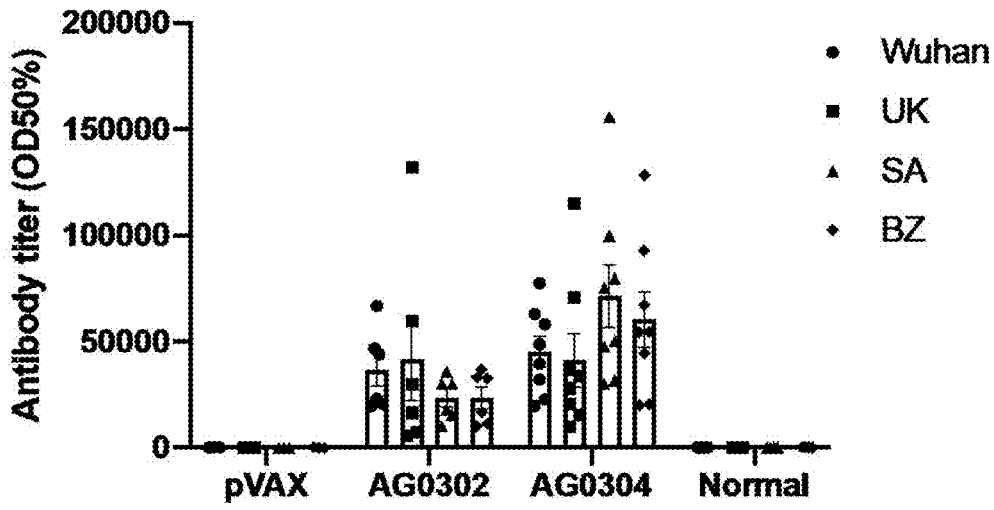
FIG. 8 shows the reaction between spike proteins and antibodies produced in rats to which the nucleic acid construct of the present invention was administered.

Results are shown in FIG. 8. In the figure, a horizontal axis indicates the types of plasmids administered to the rats from which sera were prepared (AG0302 means plasmid CO, AG0304 means plasmid SA, and Normal means the plasmid non-administration group). In the figure, Wuhan, UK, SA, and BR indicate the types of spike proteins, and mean the spike proteins of Wuhan strain, Alpha strain, Beta strain, and Gamma strain, respectively. As shown in FIG. 8, in the sera of the rats receiving plasmid CO and plasmid SA, antibodies reactive with the all spike proteins used were produced. In addition, the antibodies produced in the rats receiving plasmid SA had similar or slightly higher antibody titers against the spike proteins of Wuhan strain and Alpha strain to or than those produced by plasmid CO, while the antibodies produced in the rats receiving plasmid SA exhibited higher reactivity with the spike proteins of Bata strain and Gamma strain than those produced by plasmid CO.

Sequence Listing Free Text

SEQ ID NO: 1; An amino acid sequence of SARS-COV-2 spike protein

SEQ ID NO: 2; A nucleotide sequence corresponding to the wild-type RNA coding SARS-COV-2 spike protein SEQ ID NO: 3; A codon-modified DNA sequence coding SARS-COV-2 spike protein SEQ ID NO: 4; A full length nucleotide sequence of plasmid CO SEQ ID NO: 5; Primer CoV-S1-WT-Q1_F SEQ ID NO: 6; Primer CoV-S1-WT-Q1_R SEQ ID NO: 7; Primer CoV-S1-CO-Q3_F SEQ ID NO: 8; Primer CoV-S1-CO-Q3_R SEQ ID NO: 9; Primer GAPDH_F SEQ ID NO: 10; Primer GAPDH_R SEQ ID NO: 11; An amino acid sequence of modified SARS-COV-2 spike protein (4GP)

SEQ ID NO: 12; A nucleotide sequence coding modified SARS-CoV-2 spike protein (4GP)

SEQ ID NO: 13; An amino acid sequence of modified SARS-COV-2 spike protein (SA)

SEQ ID NO: 14; A nucleotide sequence coding modified SARS-CoV-2 spike protein (SA)

SEQ ID NO: 15; An amino acid sequence of modified SARS-COV-2 spike protein (BR)

SEQ ID NO: 16; A nucleotide sequence coding modified SARS-CoV-2 spike protein (BR)

SEQ ID NO: 17; An amino acid sequence of modified SARS-COV-2 spike protein (IN)

SEQ ID NO: 18; A nucleotide sequence coding modified SARS-CoV-2 spike protein (IN)

---

The invention claimed is:

1. A DNA encoding a coronavirus SARS COV-2 spike protein or a fragment thereof, comprising a nucleotide sequence having 950% or more identity with a nucleotide sequence shown by SEQ ID NO: 3, 12, 14, 16 or 18.

2. The DNA according to claim 1, having a nucleotide sequence shown by SEQ ID NO: 3, 12, 14, 16 or 18.

3. A nucleic acid construct containing a promoter that functions in a human and the DNA according to claim 1 operably linked to the promoter.

4. The nucleic acid construct according to claim 3, further containing a transcription termination sequence operably linked to the DNA.

5. The nucleic acid construct according to claim 3, which is incorporated into a vector.

6. The nucleic acid construct according to claim 5, which is incorporated into a vector selected from the group consisting of a plasmid vector, a phage vector and a viral vector.

7. A pharmaceutical composition comprising the nucleic acid construct according to claim 3.

8. The pharmaceutical composition according to claim 7, further comprising an adjuvant.

9. The pharmaceutical composition according to claim 7, which is a vaccine for coronavirus infection.

* * * * *